US006869390B2

(12) United States Patent
Elliott et al.

(10) Patent No.: US 6,869,390 B2
(45) Date of Patent: Mar. 22, 2005

(54) AUTOMATED IMPLANTATION SYSTEM FOR RADIOISOTOPE SEEDS

(75) Inventors: Daniel M. Elliott, Shorewood, MN (US); John J. Berkey, St. Louis Park, MN (US); George M. Hoedeman, Eden Prairie, MN (US)

(73) Assignee: Mentor Corporation, Santa Barbara, CA (US)

(*) Notice: Subject to any disclaimer, the term of this patent is extended or adjusted under 35 U.S.C. 154(b) by 95 days.

(21) Appl. No.: 10/010,968

(22) Filed: Nov. 13, 2001

(65) Prior Publication Data

US 2003/0018232 A1 Jan. 23, 2003

Related U.S. Application Data

(63) Continuation-in-part of application No. 09/587,624, filed on Jun. 5, 2000, now Pat. No. 6,537,192, and a continuation-in-part of application No. 09/587,642, filed on Jun. 5, 2000, now Pat. No. 6,616,593.
(60) Provisional application No. 60/247,229, filed on Nov. 10, 2000, and provisional application No. 60/247,482, filed on Nov. 10, 2000.

(51) Int. Cl.[7] ............................................. A61M 36/00
(52) U.S. Cl. ................................................. 600/1; 600/7
(58) Field of Search ..................................... 600/1–8, 439, 600/427, 459, 411; 128/920–924

(56) References Cited

U.S. PATENT DOCUMENTS

| 3,861,380 | A | 1/1975 | Chassagne et al. |
|---|---|---|---|
| 4,086,914 | A | 5/1978 | Moore |
| 4,150,298 | A | 4/1979 | Brault et al. |
| 4,167,179 | A | 9/1979 | Kirsch |
| 4,401,108 | A | 8/1983 | Galkin |
| 4,586,490 | A | 5/1986 | Katz |
| 4,627,420 | A | 12/1986 | Katz |
| 4,649,925 | A | 3/1987 | Dow |
| 4,673,813 | A | 6/1987 | Sanchez |
| 4,702,228 | A | 10/1987 | Russell, Jr. et al. |
| 4,759,345 | A | 7/1988 | Mistry |

(List continued on next page.)

FOREIGN PATENT DOCUMENTS

| EP | 1 070 519 A1 | 1/2001 |
|---|---|---|
| GB | 638223 | 6/1950 |
| GB | 1308041 | 2/1973 |
| WO | WO 97/22379 | 6/1997 |
| WO | WO 99/26534 | 6/1999 |
| WO | WO 99/56825 | 11/1999 |
| WO | WO 99/60921 | 12/1999 |
| WO | WO 00/48664 | 8/2000 |
| WO | WO 00/61229 | 10/2000 |
| WO | WO 01/66185 | 9/2001 |

OTHER PUBLICATIONS

Web site print–out: *Indigo Express Seeding Cartridge*, Standard Imaging, Middleton, Wisconsin, Dec. 1999.

(List continued on next page.)

*Primary Examiner*—Samuel G. Gilbert
(74) *Attorney, Agent, or Firm*—Patterson, Thuente, Skaar & Christensen, P.A.

(57) ABSTRACT

An automated implantation system assists the implantation of low dose radioisotope seeds in a patient as part of a brachytherapy procedure. A Z-axis automated motion control system and an X-Y axis automated motion control system control a needle assembly. The X-Y axis automated motion control system positions an insertion axis of the needle assembly relative to the patient. The Z-axis automated motion control system selectively moves the needle assembly along the insertion axis to implant at least one radioisotope seed. This process is repeated for a plurality of locations on a base plane perpendicular to the insertion axis. Preferably, the radioisotope seeds are contained in a replaceable cartridge and the needle assembly is also replaceable.

48 Claims, 28 Drawing Sheets

U.S. PATENT DOCUMENTS

| | | | |
|---|---|---|---|
| 4,763,642 A | | 8/1988 | Horowitz |
| 4,815,449 A | | 3/1989 | Horowitz |
| 4,851,694 A | | 7/1989 | Rague |
| 4,869,299 A | | 9/1989 | Handke |
| 4,881,937 A | | 11/1989 | Van't Hooft |
| 4,994,028 A | | 2/1991 | Leonard et al. |
| 5,030,194 A | | 7/1991 | Van't Hooft |
| 5,084,001 A | | 1/1992 | Van't Hooft |
| 5,092,834 A | | 3/1992 | Bradshaw |
| 5,103,395 A | | 4/1992 | Spako |
| 5,120,973 A | | 6/1992 | Rohe |
| 5,139,473 A | | 8/1992 | Bradshaw et al. |
| 5,147,282 A | | 9/1992 | Kan |
| 5,181,514 A | | 1/1993 | Solomon |
| 5,183,455 A | | 2/1993 | Hayman |
| 5,205,289 A | | 4/1993 | Hardy et al. |
| 5,242,373 A | | 9/1993 | Scott et al. |
| 5,272,349 A | | 12/1993 | Perry |
| 5,282,472 A | | 2/1994 | Companion |
| 5,361,768 A | | 11/1994 | Webler |
| 5,391,139 A | | 2/1995 | Edmundson |
| 5,398,690 A | | 3/1995 | Batten et al. |
| 5,415,169 A | | 5/1995 | Siczek |
| 5,460,592 A | | 10/1995 | Langton et al. |
| 5,524,180 A | * | 6/1996 | Wang et al. .................. 600/118 |
| 5,540,649 A | | 7/1996 | Bonnell |
| 5,552,645 A | | 9/1996 | Weng |
| 5,626,829 A | | 5/1997 | Kourtrouvelis |
| 5,682,892 A | | 11/1997 | Selder |
| 5,695,500 A | | 12/1997 | Taylor |
| 5,713,828 A | | 2/1998 | Coniglione |
| 5,800,333 A | | 9/1998 | Liprie |
| 5,830,219 A | | 11/1998 | Bird |
| 5,833,627 A | | 11/1998 | Shmulewitz |
| 5,834,788 A | | 11/1998 | Fu et al. |
| 5,851,172 A | | 12/1998 | Bueche et al. |
| 5,851,173 A | | 12/1998 | Dugan |
| 5,860,909 A | | 1/1999 | Mick et al. |
| 5,868,757 A | | 2/1999 | Koutrouvelis |
| 5,871,448 A | | 2/1999 | Ellard |
| 5,906,574 A | | 5/1999 | Kan |
| 5,927,351 A | | 7/1999 | Zhu et al. |
| 5,928,130 A | | 7/1999 | Schmidt |
| 5,931,786 A | | 8/1999 | Whitmore |
| 5,938,583 A | | 8/1999 | Grimm |
| 5,951,461 A | * | 9/1999 | Nyo et al. .................. 600/118 |
| 5,957,935 A | | 9/1999 | Brown |
| 5,961,527 A | | 10/1999 | Whitmore |
| 6,007,474 A | | 12/1999 | Rydell |
| 6,010,446 A | | 1/2000 | Grimm |
| 6,036,632 A | | 3/2000 | Whitmore |
| 6,048,300 A | | 4/2000 | Thornton et al. |
| 6,095,975 A | | 8/2000 | Silvern |
| 6,102,844 A | | 8/2000 | Ravins |
| 6,106,455 A | | 8/2000 | Kan |
| 6,113,529 A | | 9/2000 | Shi |
| 6,129,670 A | * | 10/2000 | Burdette et al. ............ 600/427 |
| 6,200,255 B1 | * | 3/2001 | Yu .............................. 600/1 |
| 6,206,832 B1 | | 3/2001 | Downey et al. |
| 6,213,932 B1 | | 4/2001 | Schmidt |
| 6,221,003 B1 | | 4/2001 | Sierocuk et al. |
| 6,241,706 B1 | | 6/2001 | Leschinsky et al. |
| 6,245,008 B1 | | 6/2001 | Leschinsky et al. |
| 6,256,529 B1 | | 7/2001 | Holupka et al. |
| 6,270,472 B1 | * | 8/2001 | Antaki et al. ................. 604/61 |
| 6,280,472 B1 | | 8/2001 | Boucher et al. |
| 6,311,084 B1 | | 10/2001 | Cormack et al. |
| 6,454,696 B1 | * | 9/2002 | Kindlein et al. ............... 600/7 |
| 6,540,656 B2 | * | 4/2003 | Fontayne et al. .............. 600/7 |
| 6,554,759 B2 | * | 4/2003 | Fontayne et al. .............. 600/7 |
| 6,572,526 B1 | * | 6/2003 | Ford ............................ 600/7 |

OTHER PUBLICATIONS

Web site print–out: *Seed Plan Pro*, Standard Imaging, Middleton, Wisconsin, Oct. 1999.

Web site print–out: *Seed Vac*, Standard Imaging, Middleton, Wisconsin, Oct. 1999.

Web Site, print–out: Source Holders information, Standard Imaging, Middleton, Wisconsin, 2 pgs.; copyright 1998.

Web Site print–out: *Brachytherapy Product Directory*, Med–Tec, Inc., Orange City, Iowa, 1 pg.; Mar. 31, 2001.

Brochure: *HDR 1000 Plus—Ionization Chamber*, Standard Imaging, Middleton, Wisconsin, 15 pgs.; Feb. 15, 2000.

U.S. patent application Publication No. U.S. 2001/0053870 A1; *Method for Analyzing Amount of Activity*, Loffler et al., Publication Date: Dec. 20, 2001; 35 pgs.

* cited by examiner

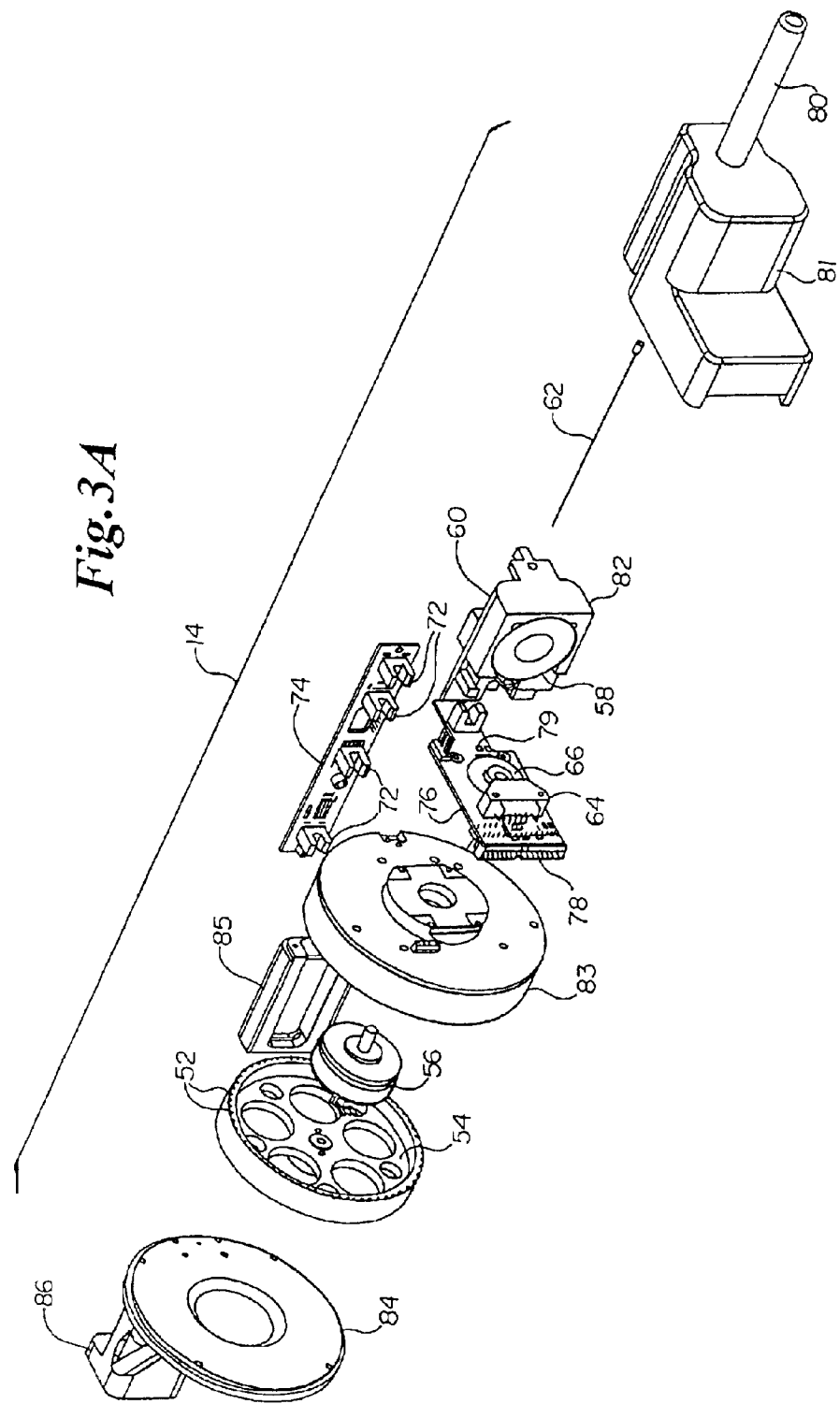

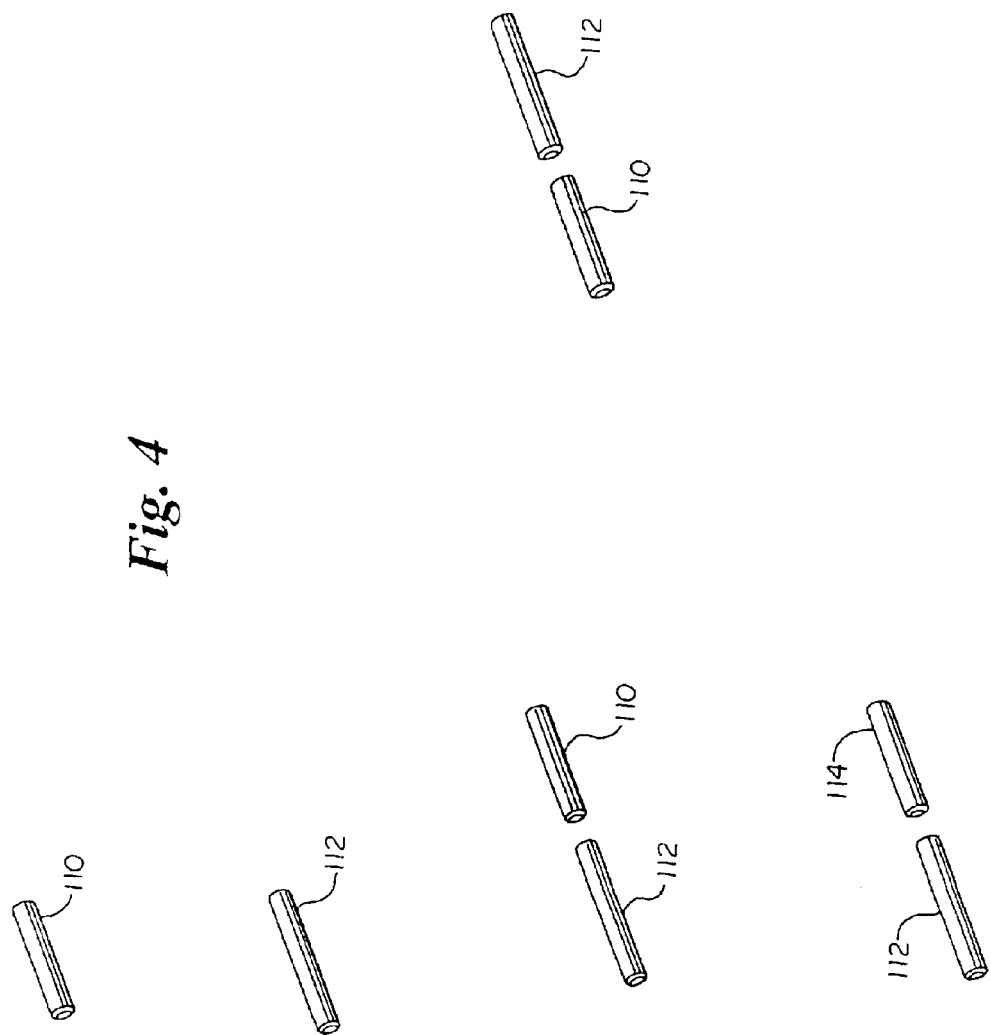

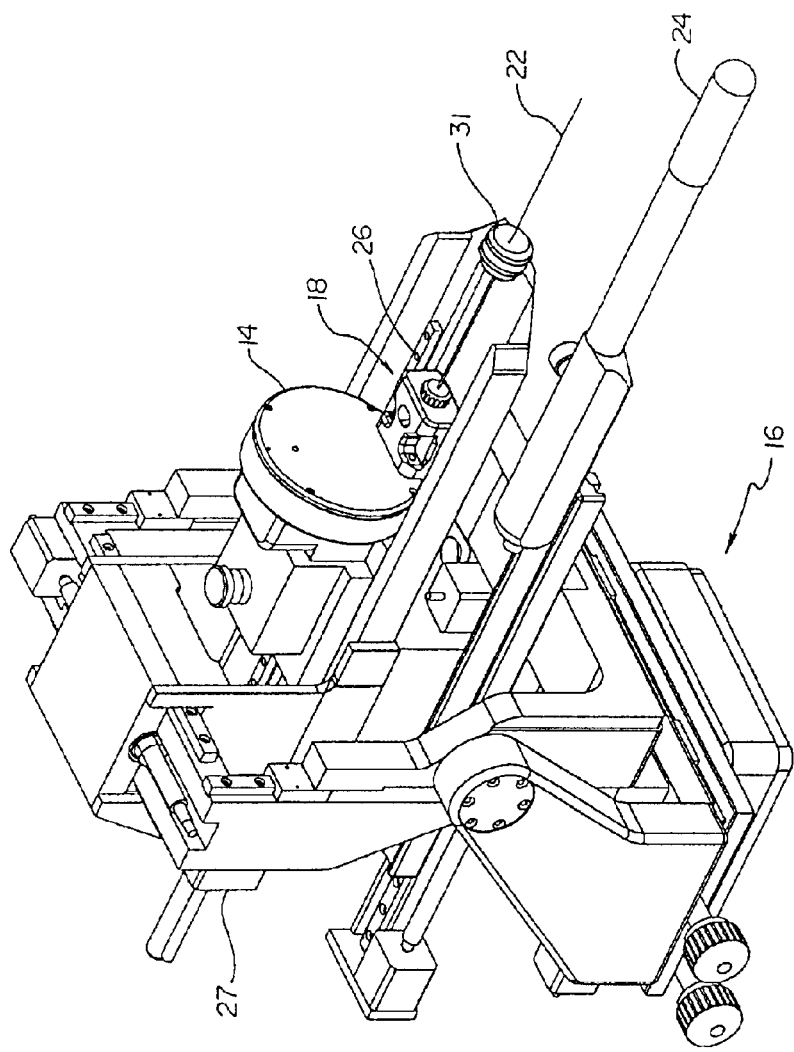

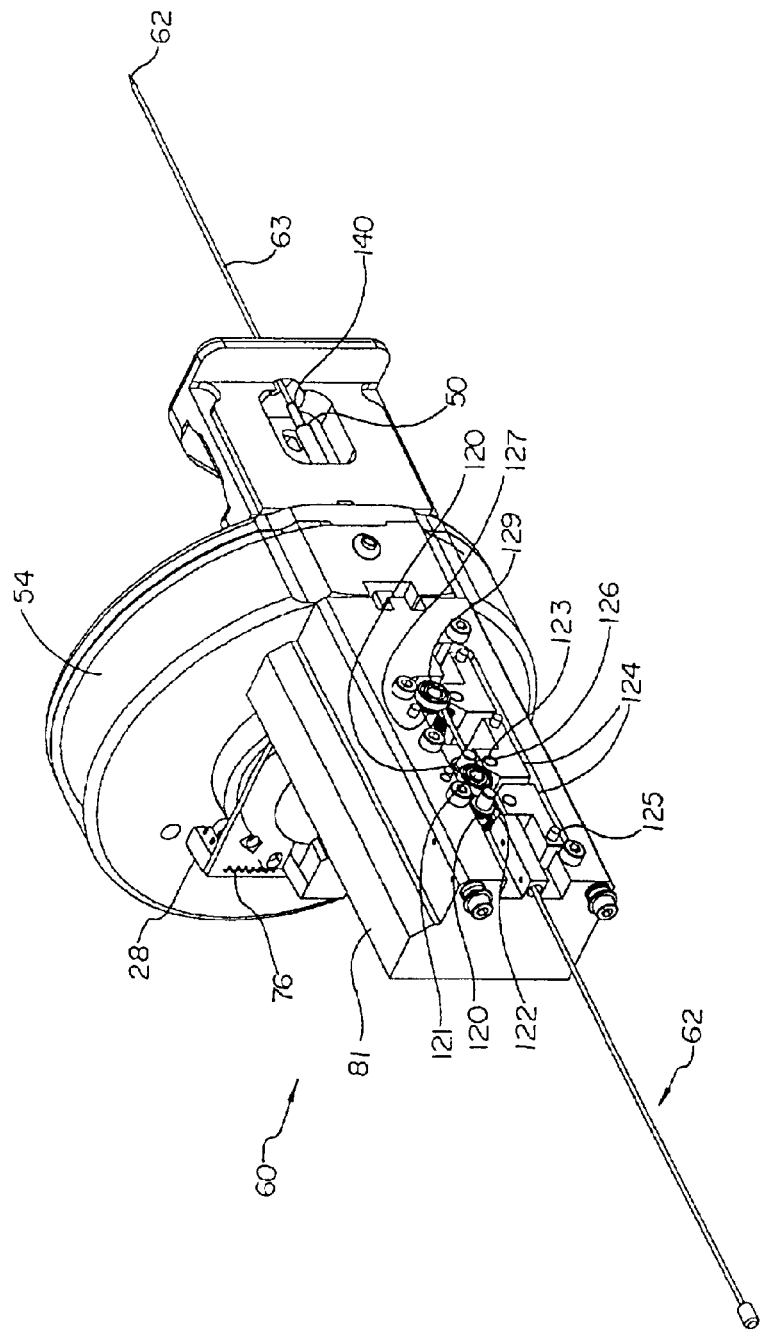

SECTION C-C

AUTOMATED IMPLANTATION SYSTEM FOR RADIOISOTOPE SEEDS

RELATED APPLICATIONS

The present application claims priority to two provisional applications filed Nov. 10, 2000, the first of which is entitled "AUTOMATED IMPLANTATION SYSTEM FOR RADIOISOTOPE SEEDS", Application No. 60/247,229, and the second of which is entitled "USER INTERFACE FOR AN AUTOMATED RADIOISOTOPE SYSTEM", Application No. 60/247,482. The present invention is a continuation-in-part of two co-pending applications that are commonly assigned to the assignee of the present invention, the first of which is entitled "AUTOMATED RADIOISOTOPE SEED LOADER SYSTEM FOR IMPLANT NEEDLES," application Ser. No. 09/587,624, filed Jun. 5, 2000, now U.S. Pat. No. 6,537,192 issued Mar. 25, 2003, and the second of which is entitled "RADIOISOTOPE SEED CARTRIDGE," application Ser. No. 09/587,642, filed Jun. 5, 2000, now U.S. Pat. No. 6,616,593 issued Sep. 9, 2003, the disclosure of both of which is incorporated by reference.

FIELD OF THE INVENTION

The present invention relates generally to the field of medical devices for handling radioisotope materials. More specifically, the present invention relates to an automated implantation system for implanting low dose radioisotope seeds in a patient as part of a brachytherapy procedure.

BACKGROUND OF THE INVENTION

The use of radioisotopes for various medical procedures such as brachytherapy and the like is well known. Such uses fall into two general categories: (i) high dose radioisotopes which are temporarily positioned in relation to a patient's body for a relatively short period of time to effect the radiation treatment; and (ii) low dose radioisotopes which are permanently implanted in a patient's body with the duration of the radiation treatment determined by the strength and half-life of the radioisotope being implanted.

High dose radioisotopes are typically implanted using a catheter arrangement and a device commonly known as an after loader that advances the high dose radioisotope located on the end of a source wire through the catheter to the desired location. Low dose radioisotopes, on the other hand, are implanted using an array of implant needles with the low dose radioisotopes being encapsulated in very small containers known as seeds that are manually loaded into a series of implant needles and then ejected to form a three-dimensional grid of radioisotopes in the patient that corresponds to a dose plan as determined by the physician.

The goal of the low dose brachytherapy procedure is to position this three-dimensional grid of radioisotopes seeds in and around a target cancerous tissue area. Each of the radioisotope seeds consists of a radioactive source such as Iodine (I-125) or Palladium (Pd-103) inside a small tube-like titanium shell that is about the size of a grain of rice. These types of low dose radioactive sources emit a very low energy radiation that is primarily absorbed by the tissue immediately surrounding the radioisotope seed. This constant low energy radiation is typically emitted by the radioisotope seeds for a period of up to six months as a way to kill the cancer cells in the target area without having to subject the patient to the discomfort and risks that often accompany high dose radioisotope procedures.

One common brachytherapy procedure is the use of low dose radioisotopes to treat prostate cancer. Although brachytherapy procedures using low dose radioisotopes can be applied to many different parts of the body, it is helpful to describe a particular treatment to gain a better understanding of these treatments. In a typical prostate cancer procedure, a predetermined number of seeds (between 1–6) are positioned within each of a series of implant needles (up to 40), with the seeds being spaced apart in each needle by small spacers. A small amount of bone wax is positioned on the tip of the implant needles to prevent the seeds and spacers from falling out until they are implanted in the patient.

The loaded implant needles are positioned at the appropriate location for insertion into the perineal area of the patient using a stand that has an X-Y coordinate grid. Each needle is manually positioned in the appropriate chamber in the grid and is inserted into the patient. An ultrasound probe is used to assist the physician in guiding each of the needles to the desired location. The seeds and spacers are delivered from the tip of the implant needle using a stylet and hollow needle arrangement where the hollow needle is preferably retracted while the stylet remains in place. When completed, the implanted seeds form a three-dimensional grid of radioisotope sources that implements a predetermined dose plan for treating the prostate cancer in the patient. For a more detailed background of the procedures and equipment used in this type of prostate cancer treatment, reference is made to U.S. Pat. No. 4,167,179.

There have been numerous developments in the design of equipment for use in low dose radioisotope procedures. U.S. Pat. Nos. 5,626,829, 5,682,892, 5,868,757, 5,931,786, 5,957,935 and 5,961,527 describe improvements in the stands and grids used to stabilize and guide the manual placement of needles during a low dose radioisotope procedure. U.S. Pat. Nos. 4,586,490 and 4,627,420 describe manually operated implanting devices that substitute for the conventional implant needles. U.S. Pat. Nos. 5,928,120 and 5,938,583 describe improvements to the conventional implant needles themselves. U.S. Pat. Nos. 4,763,642 and 4,815,449 describe a bioabsorbable carrier for implanting a string of low dose radioisotope seeds. U.S. Pat. Nos. 4,086,914, 5,242,373, 5,860,909, 6,007,474, 6,102,844, and 6,213,932 describe manual seed injector arrangements for a low dose radioisotope procedure that utilize drop-in seed cartridges or seed magazines to supply the seeds directly to an implant needle that is specifically adapted to such cartridges or magazines.

U.S. Pat. No. 6,221,003 describes an elongated cartridge with a central channel that contains a plurality of seeds interspersed with a plurality of spacers for loading a single implant needle; however, the seeds and spacers are manually loaded into the central channel using leaded gloves or tweezers. U.S. Pat. No. 6,280,472 describes an orbiturer for manually pushing seeds from a central channel into tissue such that the implants are selectably spaced from one another via a reciprocating carriage arrangement. The orbiturer also includes a mechanical detent arrangement that serves as an indicator of the number of seeds that were implanted. PCT Publ. No. WO 01/66185 describes an alternative arrangement for loading a single implant needle in which a separate seed cartridge and spacer cartridge are manually advanced into corresponding slots in a loading tube such that a manually-operated plunger can dislodge the seed and spacer from chambers in the cartridges to load the implant needle.

Over the years there also have been numerous advancements in the design of equipment for use in high dose radioisotope procedures. U.S. Pat. Nos. 3,861,380, 4,851, 694, 5,092,834, 5,120,973, 5,183,455, 5,272,349, and 5,800, 333 describe various automated afterloaders that advance a source wire carrying a high dose radioisotope at the end into a catheter system for high dose radioisotope procedures. U.S. Pat. Nos. 4,150,298, 5,147,282, 5,851,172 and 6,048, 300 describe replaceable cartridge assemblies that contain the source wire used in conjunction with specifically adapted afterloaders.

Although the use of replaceable cartridges and automated afterloaders have been well received for use in connection with high dose radioisotope procedures, the standard techniques for low dose radioisotope procedures continue to utilize a series of implant needles that are manually loaded by a radiophysicist at the hospital just prior to the time they are manually inserted by the physician. There are several reasons for why this manual process has been the standard for low dose radioisotope procedures.

The differences in the types of radioisotope sources do not favor the use of existing manual drop in cartridges for low dose radioisotope procedures. The source wires used for high dose radioisotope procedures use only one or a small number of very high power radioisotope sources having relatively long half-lives. As a result, it is cost effective and practical to provide for a cartridge arrangement for such a small number of high dose radioisotopes that can be preordered and maintained at the hospital well in advance of a procedure. In contrast, low dose radioisotope procedures have relatively short half-lives of the radioisotopes and it is preferable that the radioisotope seeds be sent to the hospitals just prior to their use. Because the number of radioisotope seeds varies from procedure to procedure depending upon the dose plan, and because the cost of each low dose radioisotope seed is significant, it is not cost effective to order many more radioisotope seeds than will be used in a given procedure.

It is important to minimize the time of the procedure, both in terms of the exposure time of the physician to the low dose radioisotope seeds and in terms of the total time of the procedure from the economics of medical practice. In the case of brachytherapy treatment for prostate cancer, it is also advantageous to complete the procedure as quickly as possible because the prostate gland can swell during the procedure, further complicating the implantation process. The existing drop-in cartridge and seed magazine manual systems described above for low dose radioisotope procedures generally require a longer time to perform the implant procedure than when conventional preloaded implant needles are used. This is because the radioisotope seeds are manually implanted one-by-one, rather than being delivered simultaneously as a group from a preloaded needle. The manual one-by-one techniques also can require more care and precision to insure that all of the seeds for a given row are actually implanted in that row.

Due to the large number of low dose radioisotope seeds used in a given procedure (typically up to 150), the requirement that a radiophysicist at the hospital take a set of sample measurements of the strength of the radioisotope seeds to confirm that the seeds meet the requirements specified by the dose plan, and the need for the implanting physician to be able to modify the dose plan at the time of implant, it is generally considered that the flexibility afforded by manually loading the implant needles just prior to the operation provides the best possible treatment procedure for the patient and the most economically efficient procedure for the hospital.

More recently, systems that attempt to integrate the diagnostic process of establishing a dose plan using an ultrasound probe with a manual implant needle grid have been proposed. The process of establishing a dose plan for brachytherapy treatment is described, for example, in U.S. Pat. No. 6,095,975. In U.S. Pat. No. 5,871,448, a manual stepper arrangement for positioning the ultrasound probe is described. In U.S. Pat. No. 6,206,832, an apparatus for merging multiple ultrasound image to assist in guiding implant needles is described.

In U.S. Pat. No. 6,129,670, an automated arrangement is described for utilizing the ultrasound probe to generate ultrasound image data that is used to generate a translucent volume image of the patient's body and the prostate over which an image of the implant needles can be superimposed. One embodiment of this patent briefly describes an automated system for loading radioisotope seeds into implant needles based on a clinical plan that enables rapid treatment based on substantially real-time preplanning using rapid patient organ evaluation. In this embodiment, a gravity fed bin arrangement selectively drops seeds into the rear end of a vertically oriented needle. A pair of micro-controllers communicates with the computer that generated the dose plan to be the dose plan and control the dropping of the seeds and spacers into the rear end of the needle by using an optical sensor positioned along the passageway through which the seeds are dropped to monitor loading of each seed into the needle. Although the needle loading is proposed to be automated in this manner, the implantation of the loaded needles is accomplished manually using a conventional needle grid arrangement.

A modular device for implanting radioactive seeds through a needle implanted in the body is described in EP 1 070 519 A1. An electronic control device controls a pushing drive, a seed supply container, a spacer supply container and a multi-channel holder for seed-spacer trains. A tube connects the multi-channel holder and the needle through which the seed-spacer trains are pushed by a wire in order to implant them in the body, with the wire remaining in place while the needle is withdrawn. In one embodiment, the seed-spacer trains are loaded and implanted by a single unit. In another embodiment, the seed-spacer trains are preloaded into the multi-channel holder by a loading unit and then the multi-channel holder is then transferred to an implantation unit. In this embodiment, a microprocessor is used to control the seed loading unit in response to a therapy planning program. Like U.S. Pat. No. 6,129,670, the loading of seeds and spacers to form the seed-spacer trains in EP 1 070 519 A1 is accomplished directly in response to the therapy planning program executed that determines how the needles are to be placed in the prostate and how many radioactive seeds are to be placed in what order in each of the needles.

Other uses of automated arrangements for positioning ultrasound probes or for controlling biopsy needles have been proposed. U.S. Pat. Nos. 4,649,925, 5,181,514, 5,282, 472, 5,361,768, 5,540,649, and 5,552,645 describe the use of automated arrangements for positioning of ultrasound probes. These automated arrangements typically include a stepper motor for advancing and retracting the ultrasound probe within the rectum and a rotational control for rotating the probe once in position within the rectum. U.S. Pat. Nos. 5,398,690, 5,415,169, and 5,830,219 describe automated biopsy arrangements in which a biopsy needle is inserted under automated control to obtain and extract a biopsy sample. These automated systems also include a single linear motion control and a rotational component control, and have an additional angulation control that controls the orientation of the needle upon insertion.

More complicated and expensive three-dimensional automated control systems for surgical instruments also have been developed. U.S. Pat. Nos. 5,540,649 and 5,695,500 describe examples of automated surgical systems that feature multiple joints and arms to allow for control of motion in all three axis of a surgical instrument positioned at the working end of these systems. The complexity and expense of these three-dimensional control systems have generally precluded their use in connection with positioning systems for ultrasound probes and biopsy needles.

Despite these improvements, the manual processes for low dose radioisotope procedures remains the standard for the reasons described above. It would be advantageous to provide for an automated implantation system for implanting low dose radioisotope seeds in a patient as part of a brachytherapy procedure that could overcome these problems and enhance the safety and efficiency of this process.

SUMMARY OF THE INVENTION

The present invention is an automated implantation system for implanting low dose radioisotope seeds in a patient as part of a brachytherapy procedure. A Z-axis automated motion control system and an X-Y axis automated motion control system control a needle assembly. The X-Y axis automated motion control system positions an insertion axis of the needle assembly relative to the patient. The Z-axis automated motion control system selectively moves the needle assembly along the insertion axis to implant at least one radioisotope seed. This process is repeated for a plurality of locations on a base plane perpendicular to the insertion axis.

A seed cartridge contains at least a plurality of radioisotope seeds preloaded into the cartridge, the needle assembly, and structure for mounting the seed cartridge and the needle assembly in the carrier structure. An implantation station has a base structure that initially positions the insertion axis relative to the patient. Preferably, the base structure includes a base, a moveable assembly that includes the insertion axis and is orientable independently of the base, and a stand operably connected between the base and the moveable assembly. Cartridge receiving structure is defined along a portion of the insertion axis in the moveable assembly to receive the cartridge.

The Z-axis automated motion control system selectively moves the needle assembly along the insertion axis and selectively advances at least one radioisotope seed from the cartridge along the insertion axis when the cartridge is positioned in the cartridge receiving structure. Preferably, the X-Y axis automated motion control system selectively moves the moveable assembly in the plane perpendicular to the insertion axis. A computer processor operably connected to at least the Z-axis automated motion control system and the X-Y axis automated motion control system has a user interface that displays information about the automated implantation system and accepts commands from a user to control the process of implanting the plurality of radioisotope seeds.

BRIEF DESCRIPTION OF THE DRAWINGS

FIGS. 3A and 3B are exploded perspective views of the preferred embodiment of the replaceable cartridge of FIG. 1.

FIG. 4 is a schematic representation of the various combinations of radioisotope seeds and spacers as stored in the rotatable drum of the preferred embodiment of the replaceable cartridge of FIG. 3.

FIG. 5 is a detailed perspective view of the moveable assembly of the preferred embodiment of the present invention.

FIG. 6 is a detailed perspective of the replaceable cartridge with a needle assembly in place.

DETAILED DESCRIPTION OF THE PREFERRED EMBODIMENT

Figure 1:
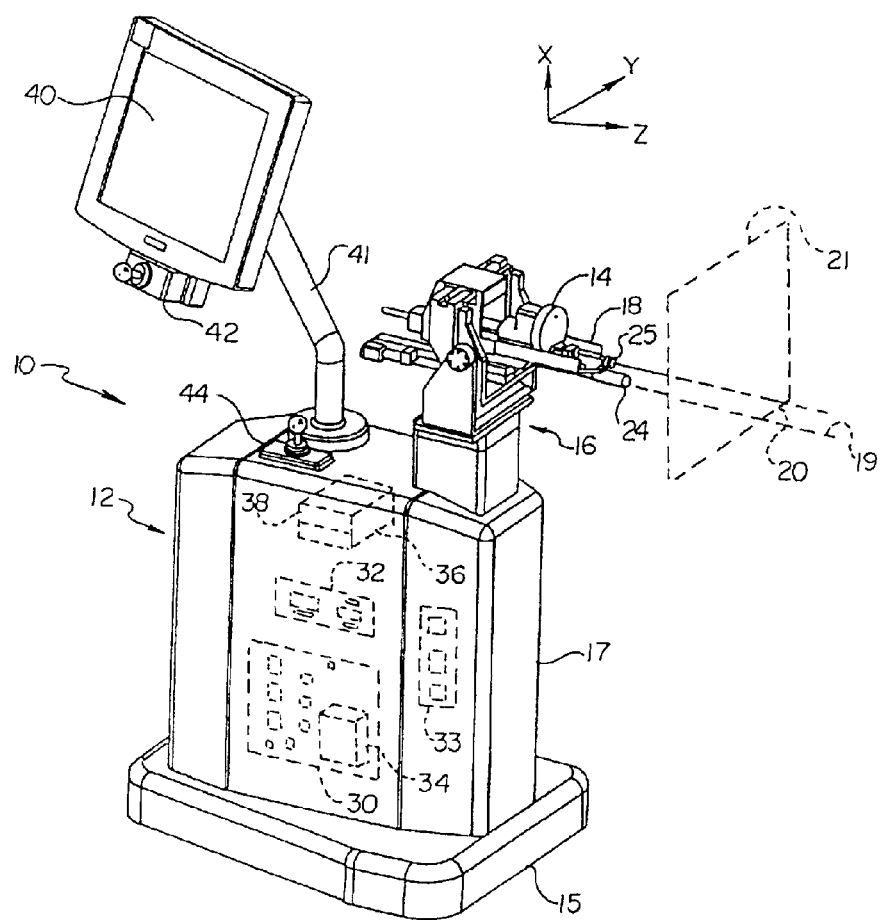
FIG. 1 is a perspective view of a preferred embodiment of the automated implantation system for implanting low dose radioisotope seeds and showing the preferred embodiment of the replaceable cartridge of the present invention in place within the automated implantation system.

Referring to FIG. 1, an automated implantation system 10 for implanting low dose radioisotope seeds into a patient is comprised of an implantation station 12 into which a replaceable cartridge 14 may be positioned. A moveable assembly 16 is positioned in an appropriate relation to the patient (not shown) for the brachytherapy procedure. A cartridge receiving structure 18 is defined in the moveable assembly 16 along an insertion axis 20. A needle assembly 22 is moveable along the insertion axis 20 (in a Z direction) and in a plane 21 defined perpendicular to the insertion axis (in both X and Y directions) by an automated motion control system as will be described. Preferably, an ultrasound probe 24 also carried by the moveable assembly 16 is moveable along an axis parallel to the insertion axis 20.

Figure 2:
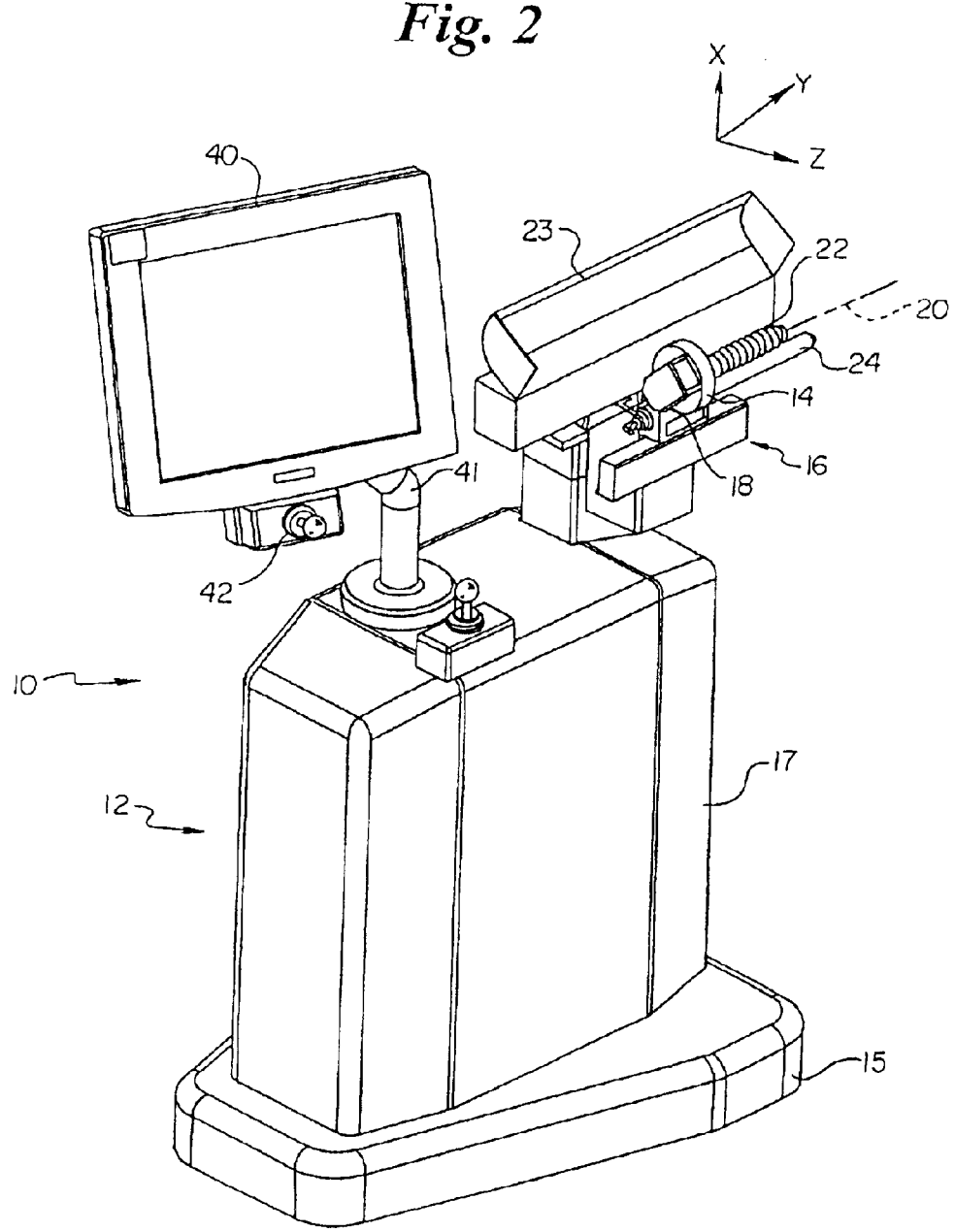
FIG. 2 is a perspective of an alternate embodiment of the automated implantation station with an enclosure over the moveable assembly.

Preferably, the implantation station 12 is a standalone unit that includes a base 15 and a stand 17 supporting the moveable assembly 16 relative to the base 15 (as shown in FIG. 1) and a hinged cover 23 (as shown in FIG. 2) for the moveable assembly 16. All of these components are preferably formed of molded plastic or metal. Although the implantation station 12 will be described as a standalone unit providing its own support and housing arrangements, it will be understood that the automated implantation system 10 of the present invention is equally applicable to an arrangement in which the moveable assembly 16 would be mounted on a table or other platform or where the moveable assembly 16 is hung from an arm or ceiling. Similarly, while the preferred embodiment of the automated implantation system 10 includes all of the electronics, software, controls, and displays for operating the implantation station as part of a single unit, the present invention contemplates that the various functions of these components could be performed by separate devices in separate housings.

A computer processor 30 for the automated system is preferably a motherboard having a microprocessor, internal bus, a PCI-compatible bus, DRAM and EPROM or battery backed SRAM, with appropriate external interfaces or mated PC boards for a video interface, multiple channel IDE interfaces, a floppy disk interface, an ethernet interface, COM and LPT interfaces, an external bidirectional parallel port and a serial port. An automated motion control system 32 is preferably a Galil motion controller available from Galil Motion Control Inc. that interfaces to the computer processor 30 via the PCI-compatible bus. The automated motion control system 32 with appropriate software drivers provides all functionality for the lowest level control of stepper motor position and feedback sensors. A hard disc drive 34, floppy disk drive or high density removable media drive 36 and CD or CD-RW drive 38 are also provided for storing data and information to be used by the automated implantation system 10.

A video display 40 that operates as the primary user interface is preferably a 1280 by 1024 resolution flat 18.1 inch flat panel LCD with a resistive touch-screen, such as are available from National Display Systems. In this embodiment, an arm structure 41 positions the display 40 in a position convenient for the user. Alternatively, a conventional non-touch-screen video display and mouse, keyboard or similar input devices could also be provided. Preferably, two separate joy stick controls 42, 44 are provided as direction control input mechanisms to allow a user to control at least the Z-axis direction of the automated motion control system 32. In this embodiment, the joy stick control 42 is preferably a single Z-axis control input located near the video display 40 that controls the advancement and retraction of the needle assembly 22 along the insertion axis 20. The joy stick control 44 is a dual axis control input located on the stand 17 that can selectively control a variety of other automated motion functions for the implantation station 12, including, for example, fine movement of the insertion axis 20 to different locations in the X-Y plane 21, as well as gross movements of the moveable assembly 16 relative to the patient. It will be understood that a variety of alternative direction control input mechanisms could also be utilized with the present invention, such as icon controls displayed on the video display 40, voice activated controls processed by the computer processor 30, or switches, slides, dials, or similar mechanical controls.

Figure 17:
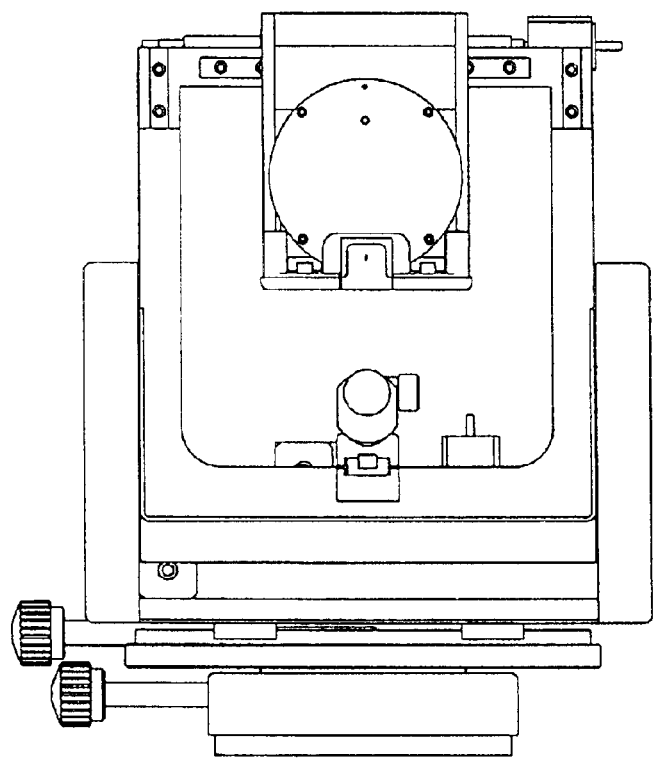
Figure 18:
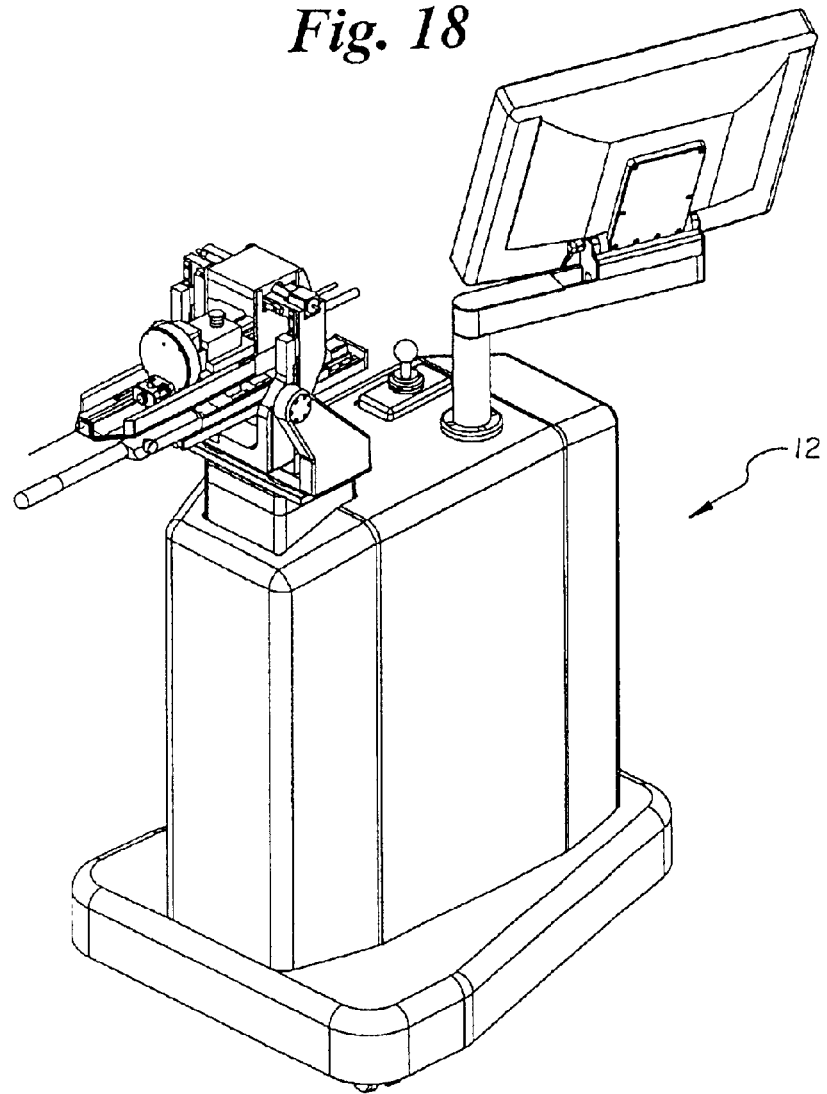
FIGS. 18, 19, and 20 are three different perspective views of a preferred embodiment of the implantation station of the present invention.
Figure 19:
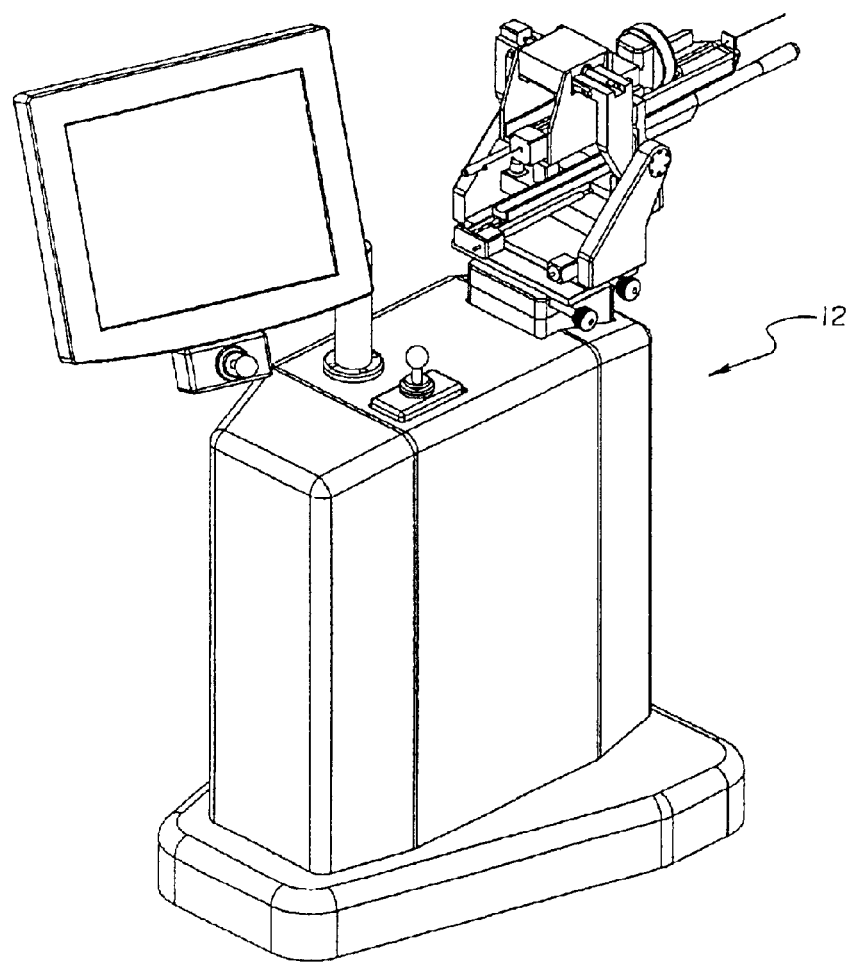
Figure 20:
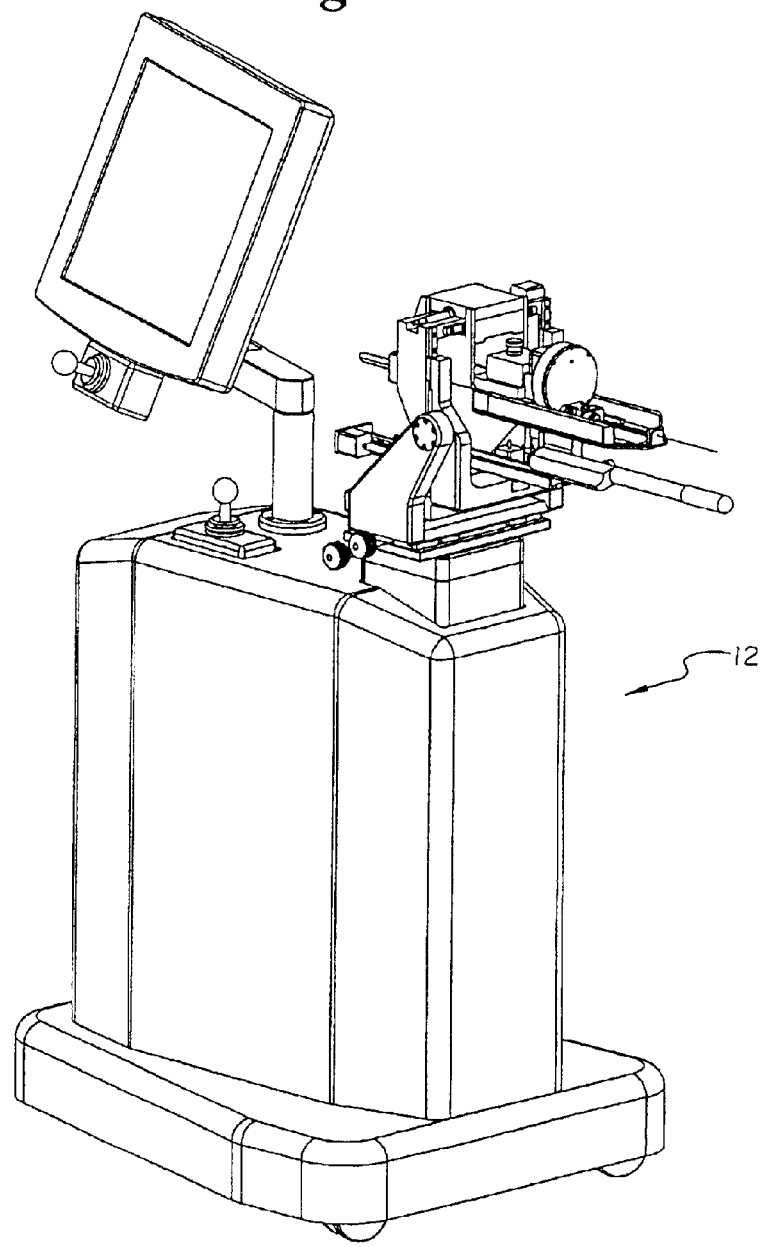

Referring specifically to FIG. 5, the cartridge receiving structure 18 of the preferred embodiment will be described. The cartridge receiving structure 18 includes a U-shaped bracket 25 (FIG. 17) that rides on a pair of rails 26 with each rail 26 of the bracket preferably being driven by one of a pair of synchronized stepper motors 27. The pair of brackets 25 and corresponding pair of stepper motors 27 are preferably utilized to control any potential skew of the cartridge 14 as it is moved along the insertion axis 20. Alternatively, a single stepper motor and single rail, a linear screw drive, a rodless cylinder, or any number of other motion arrangements could be provided to drive the cartridge 14.

Once in position, the implantation station 12 locks the cartridge 14 in place using an electrical solenoid 29 to prevent inadvertent removal of the cartridge 14 during operation of the automated system 10. Locking is initiated automatically once the presence of a cartridge 14 has been detected in the cartridge receiving structure 18 and the user has initiated an implantation operation via display 40. Unlocking the cartridge is initiated by the user selecting a remove cartridge operation via display 40, but only after computer processor 30 has confirmed completion of any critical motions that are part of the implantation operation and removed power to the cartridge 14. Preferably, the only other interface between the cartridge 14 and the cartridge receiving structure 18 is a multiple pin-type electrical connector 28.

Preferably, a disposable guide bushing 31 is utilized at the distal end of the cartridge receiving structure 18 to house the distal end of the needle assembly 22 while the proximal end of the needle assembly 22 can be attached to the cartridge 14. In one embodiment, the needle assembly 22 is prepackaged in the place within the guide bushing 31 and need only be screwed onto or otherwise connected to the cartridge 14. This allows the guide bushing 31 to be disposable. In this embodiment, the guide bushing 31 has appropriate mating structure within the cartridge receiving structure 18. Preferably, a condom or other disposable membrane would cover the exposed portion of the needle assembly 22 to reduce the possibility of contamination by body fluids. In an alternate embodiment, the needle assembly 22 could be threaded into a guide bushing that was part of the moveable assembly 16. In still another embodiment, a carrier structure could be created to hold both the cartridge and the needle assembly in a single arrangement that would be loaded together into the implant station.

As the stepper motors and associated encoder discs are contained within the cartridge 14, the need for extremely tight tolerance matches between the cartridge receiving structure 18 and the cartridge 14 is minimized. In addition to the necessary control and sensor signals, the connector 28 includes a ground and power connection to provide power to the cartridge 14. The presence of cartridge 14 in cartridge receiving structure 18 is also detected via a contact on connector 28. Although an arrangement using a bracket 25 and pair of guide rails 26 that is driven by a stepper motor 27 and is connected by the electrical connector 28 and locked by an electrical solenoid 29 is the preferred embodiment for interfacing the cartridge 14 with the cartridge receiving structure 18, it will be recognized that many other structures, such as channels, latches, pivoting arrangements, ball and detent locks, and orientations, such as horizontal or vertical, and connectors, such as optical, infrared, RF, slide contacts, array contacts or the like, could be used to accomplish the same function of interfacing the cartridge 14 with the cartridge receiving structure 18.

Figure 3B:
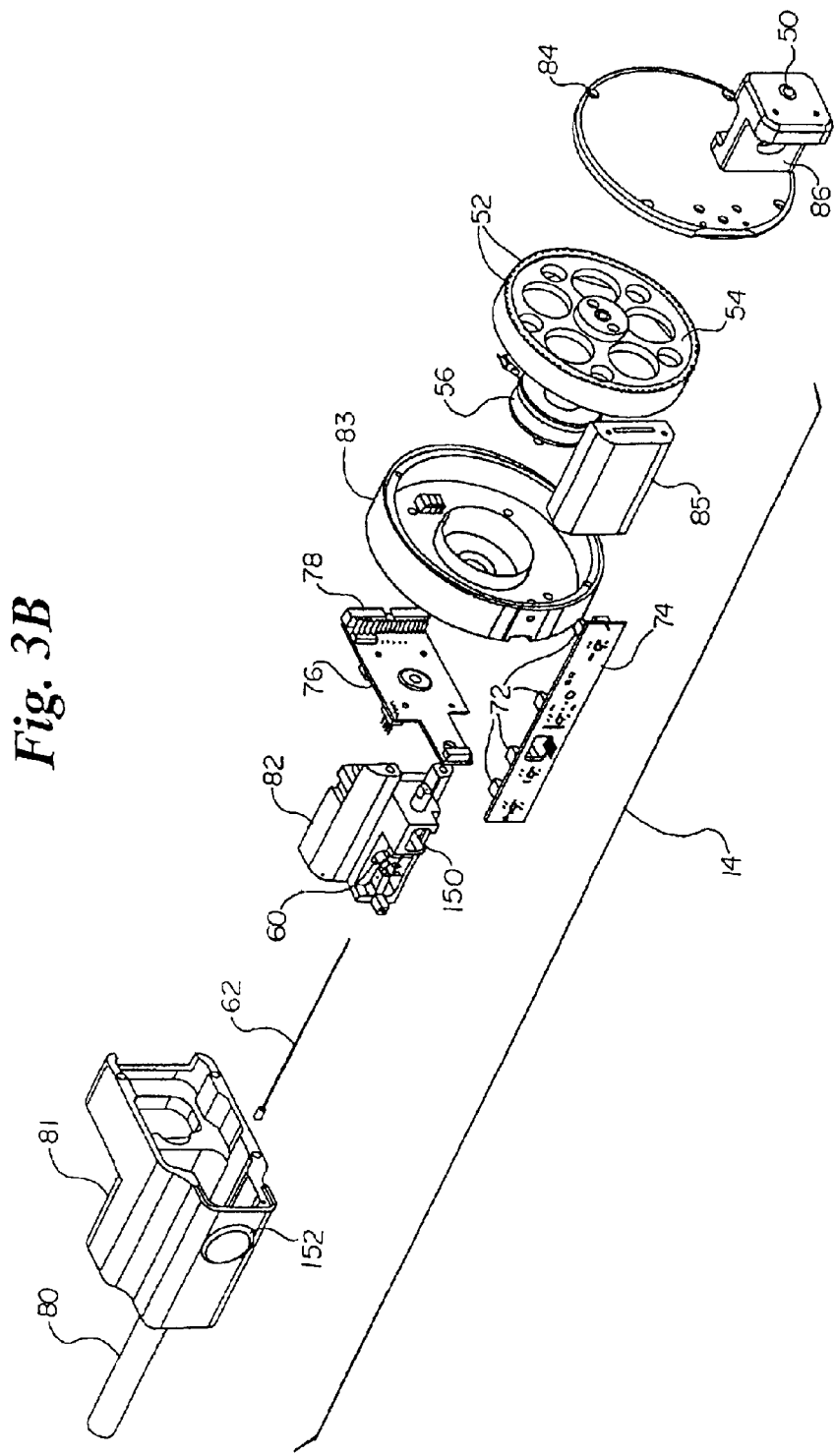

Referring now to FIGS. 3A and 3B, one embodiment of the cartridge 14 contains a plurality of radioisotope seeds and a plurality of spacers preloaded into the cartridge. The cartridge 14 has at least one aperture 50 into which at least a portion of the needle assembly 22 is positioned. Preferably, the radioisotope seeds and spacers are loaded into holes or chambers 52 located around the periphery of a rotatable drum 54. In this embodiment, the cartridge 14 includes a pair of stepper motors within the cartridge. A first stepper motor 56 rotates the rotatable drum 54. It will be seen that stepper motor 56 preferably drives rotatable drum 54 directly without any intervening gearing arrangement.

A second stepper motor 58 has a capstan assembly 60 that rotates in engagement with a trochar needle 62 to slide the trochar needle 62. For the rotatable drum 54, an encoder detector 64 detects the position of a corresponding encoder disc 66 that is then communicated back to automated motion control system 32 (FIG. 1). Preferably, the stepper motor and encoder are selected such that the stepper motor steps in full steps with relation to the distance between chambers around the periphery. The alignment of the aperture 50 to the chambers 52 in the drum 54 is preferably initially accomplished at the time of assembly. It will also be seen that other motor drives other than stepper motors could be used with equivalent success in the present invention, such as servo motors, worm driven motors, or DC motors with appropriate indexing control.

In an alternative embodiment, an encoder with a higher degree of resolution can be used and the stepper motor can be incremented in less than full steps. In this embodiment, a first encoder for the rotatable drum 54 generates a positional feedback signal of an index of the chambers of the rotatable drum 54 relative to the line of travel of the capstan assembly 60, and a second encoder with a second encoder disc for the capstan assembly 60 that generates a positional feedback signal of a position of the elongated member along the line of travel.

Referring to FIG. 6, the needle assembly 22 is preferably comprised of the trochar needle 62 coaxially located within a canula 63. At least the trochar needle 62 is preferably replaceably mounted in the cartridge 14 to permit removal and replacement of the trochar needle 62 when the procedure is completed. Preferably, the canula 63 is also replaceably mounted to the cartridge 14 to permit removal and replacement of the canula 63 when the procedure is completed. Although a trochar needle 62 within a canula 63 is the preferred embodiment of needle assembly 22, it will be recognized that other embodiments of the needle assembly 22 could be provided, such as a coaxial arrangement of a push rod inside an outer needle where the outer needle does the cutting.

Referring again to FIG. 3, a series of position sensors 72 are positioned in line with the trochar needle 62 to detect the travel of trochar needle 62 as it is driven by capstan system 60 through its line of travel. The sensors 72 are connected to sensor circuitry 74 to communicate this position information to the automated motion control system 32. Each of the encoder detector 64 and sensor circuitry 74 are electrically connected to a circuit board 76 which has an appropriate connector 78 for mating with and connecting with a corresponding connector 28 (FIG. 5) in the cartridge receiving structure 18 of the housing 12.

Preferably, the circuit board 76 is provided with an electrically erasable programmable read-only memory (EEPROM) 79 or similar non-volatile memory to store parameters and other data that are unique to the particular cartridge 14 and to the particular patient and dose plan that has been developed for that patient. The contents of EEPROM 79 are set up initially during loading and calibration of the cartridge 14 at the factory. These contents are updated by the automated system 10 so as to continually reflect the current state of the cartridge 14. For example, when the radioisotope seeds and/or spacers are ejected from a given chamber 52, then the data on the EEPROM 79 is updated to reflect that the given chamber 52 no longer contains any radioisotope seeds and/or spacers. Preferably, the EEPROM 79 is capable of storing patient and hospital identification information, as well as seed inventory and manufacture information. Optionally, the EEPROM 79 could also store the predetermined dose plan for the particular patient.

In the preferred embodiment, various housing elements enclose the cartridge 14 to create a single, enclosed drop-in cartridge to simplify operation and handling of the cartridge as shown in FIG. 3. Preferably, the various housing elements are formed of machined stainless steel to enhance the protective aspect of the housing. Alternatively, the housing could be formed of materials other than stainless steel. For example, the housing elements could be molded plastic with appropriate pieces having an internal lead lining or the like to provide sufficient shielding. Although the preferred embodiment is described as a single, enclosed drop-in cartridge, it will be understood by those skilled in the art that some or all of the functional components of cartridge 14 may be separately enclosed or left unenclosed and operably connected together to accomplish the same functionality, such as allowing for mating with the cartridge receiving structure 18 and protecting movement of the trochar needle 62 along its line of travel.

In the embodiment of the cartridge 14 as shown in FIG. 3, a sleeve 80 encloses the rearward travel of trochar needle 62. Cover 81 is a one-piece unit that covers the capstan assembly 60 and its associated components. A capstan motor mount 82 provides a mounting base for most of the main components of cartridge 14, including circuit board 76 and encoder detector 64. Housing 83 houses the stepper motor 56 and the rotatable drum 54. A cover plate 84 mounts to the housing 83. The motor mount 82 and the cover 81 are secured by internal screws (not shown) that are accessed when the cover plate 84 is removed. A front plate 85 covers the circuit board 76 and is also mounted with screws between cover plate 84 and cover 81. A needle housing 86 is also screwed on to the cover plate 84 and includes the aperture 50 through which the needle assembly 22 accesses the cartridge 14.

FIGS. 6, 10, 11, 24, and 25 show various views of a preferred embodiment of the cartridge 14 that is similar to the cartridge 14 as described in connection with respect to FIG. 3. The primary differences in this embodiment relate to the nature of the capstan assembly 60 for driving the trochar needle 62 and the construction of the portion of the cartridge 14 that attaches to the needle assembly 22. Due to the desire to location the insertion axis 20 as closely as possible to the axis of the ultrasound probe 24, the cartridge 14 of the preferred embodiment of the present invention minimizes the depth of the bottom structure of the cartridge 14. This allows the cartridge 14 to sit low within the cartridge receiving structure 18 and immediately above the ultrasound probe 24. Consequently, the aperture 50 is preferably located on the very bottom of the drum 54. The structure of the cartridge 14 at the front of the cartridge that attaches to the needle assembly 22 is preferably made as wide as the structure at the rear of the cartridge which houses the stepper motor. The only depth created on the bottom of the cartridge 14 is the depth necessary for the circuit board connecting the sensor 72 and an associated cover.

In addition to the advantages afforded by constructing cartridge 14 as a single, enclosed drop-in cartridge, the preferred embodiment of cartridge 14 is designed with minimum piece parts to allow for easy disassembly and sterilization to allow for potential re-use. Once the various covers and circuit assemblies are removed, the remaining portions of cartridge 14 are cleaned with alcohol or hydrogen peroxide to remove bioburden. When reassembled, the entire cartridge 14 is preferably sterilized with a gas sterilization technique. The ease of disassembly also provides a convenient mechanism by which emergency removal of the radioisotope seeds can be accomplished, simply by removing cover plate 84 and dumping the radioisotope seeds and spacers into an appropriate container.

The use of a rotatable drum 54 also affords important advantages to the preferred embodiment of the present invention. The positioning of the chambers 52 around the periphery of drum 54 reduces the concentration of radiation sources at any given point and provides an optimum separation of radioisotope seeds from each other, thereby enhancing the safety of cartridge 14.

In the preferred embodiment, each chamber 52 is long enough to accommodate any of a combinatorial set of radioisotope seeds, spacers and plugs. As shown in FIG. 4, various combinations of radioisotope seeds 110, full-length spacers 112, and partial-length spacers 114 which can serve as blanks can be positioned within a given chamber 52. In this embodiment, the length of one radioisotope seed 110 or one blank 114 is 4.5 mm and the length of one full-length spacer 112 is 5.5 mm. As will be apparent, the selection of the lengths of each of the seeds 110, and spacers 112, 114 allows for various combinations to be utilized that have the same overall length when positioned in an implant needle of 10 mm for seed and spacer. The particular combination of each for a given cartridge is optimally determined at the time that the cartridge 14 is preloaded in accordance with a predetermined dose plan. This information can then be utilized by the automated station 10 to load the implant needles in accordance with that predetermined dose plan.

In the preferred embodiment, the rotatable drum 54 is provided with 200 chambers 52 spaced equidistant about the periphery of the rotatable drum 54. The optical encoder disc 66 preferably has 400 or 1600 lines of resolutions that yield a resolution of 2 or 8 counts per chamber 52. In an alternate embodiment with higher resolution as previously described, 72,000 lines of resolution are used which yields a resolution of 360 counts per chamber 52. A home reference is provided by an index channel on the encoder disc 66. The alignment of the aperture 50 to the chambers 52 in the drum 54 using the index channel is preferably accomplished at the time of assembly. In the high-resolution embodiment, an offset to a first chamber location clockwise from the home reference is stored as a parameter for the cartridge 14 to allow for individual cartridge tolerance calibration. Alternatively, an optical sensor could be used to locate the center of a chamber 52 for purposes of calibrating an index.

In operation, the automated motion control system 32 uses the first stepper motor 56 and encoder detector 64 to establish a reference to the first seed drum chamber 52. Motion of the drum 54 may take place bidirectionally (i.e., clockwise or counterclockwise) and as rapidly as possible in order to move to the nearest desired chamber location as determined by the computer processor 30 and automated motion control system 32 in the shortest possible time. When requested by the computer processor 30, the automated motion control system 32 will index to the center of the desired chamber location in preparation for transfer of the contents of that chamber 52 to the implant needle. The drum 54 will remain at this location until it is commanded to a new position.

When a request for a seed transfer is generated by the computer processor 30, the automated motion control system 32 activates the capstan assembly 60 to retract the trochar needle 62, thereby allowing the drum 54 to be rotated freely. When the drum 54 has been indexed to the desired chamber location, the automated motion control system 32 instructs the second stepper motor 58 to move the trochar needle 62 forward to push the contents of the chamber 52 out of the drum 54 and into the needle assembly 22.

The trailing one of the position sensors 72 is provided along the path of material transfer to allow for detection of the leading edge of the contents with relation to the tip of trochar needle 62. As the contents of a given chamber 52 are moved by the position sensor 72, the total length of the contents may be determined. This configuration allows for a verification of the length of the contents of a given chamber 52 with the information the automated system has about what should be in that chamber 52 to prevent potential implants of the wrong seeds. In the event of an early or late activation of the sensor 72 by the tip of the trochar needle 62 in relation to the expected activation based on the anticipated length of the contents of that given chamber 52, an alarm or error message would be passed to the computer processor 30.

Although the drum 54 has been described as the preferred embodiment of the positional member of the cartridge 14 with its movement controlled by first stepper motor 56, it should be understood that other forms of this positional member and other motor arrangements would also work within the scope of the present invention. For example, the positionable member could be an X-Y grid of chambers with a pair of stepper motors used to drive the grid in X-Y directions to position the desired chamber in line with the aperture 50 and trochar needle 62. Although stepper motors, such as stepper motor 56, and encoders, such as encoder disc 66 are a convenient and economical manner of implementing the present invention so that it may be controlled by an external microprocessor arrangement, it will be recognized that other arrangements such as gears, drive belts and clutched motor shafts could be used in place of the stepper motor, and that contact sensors, optical sensors or registry from a known starting point could also be used in place of the encoder. It will also be seen that while the preferred embodiment interfaces with an external microprocessor, it would also be possible to incorporate a microprocessor into the cartridge itself and to communicate externally by telecommunications, radio communications or the like, instead of by electrical connectors.

Figure 25:
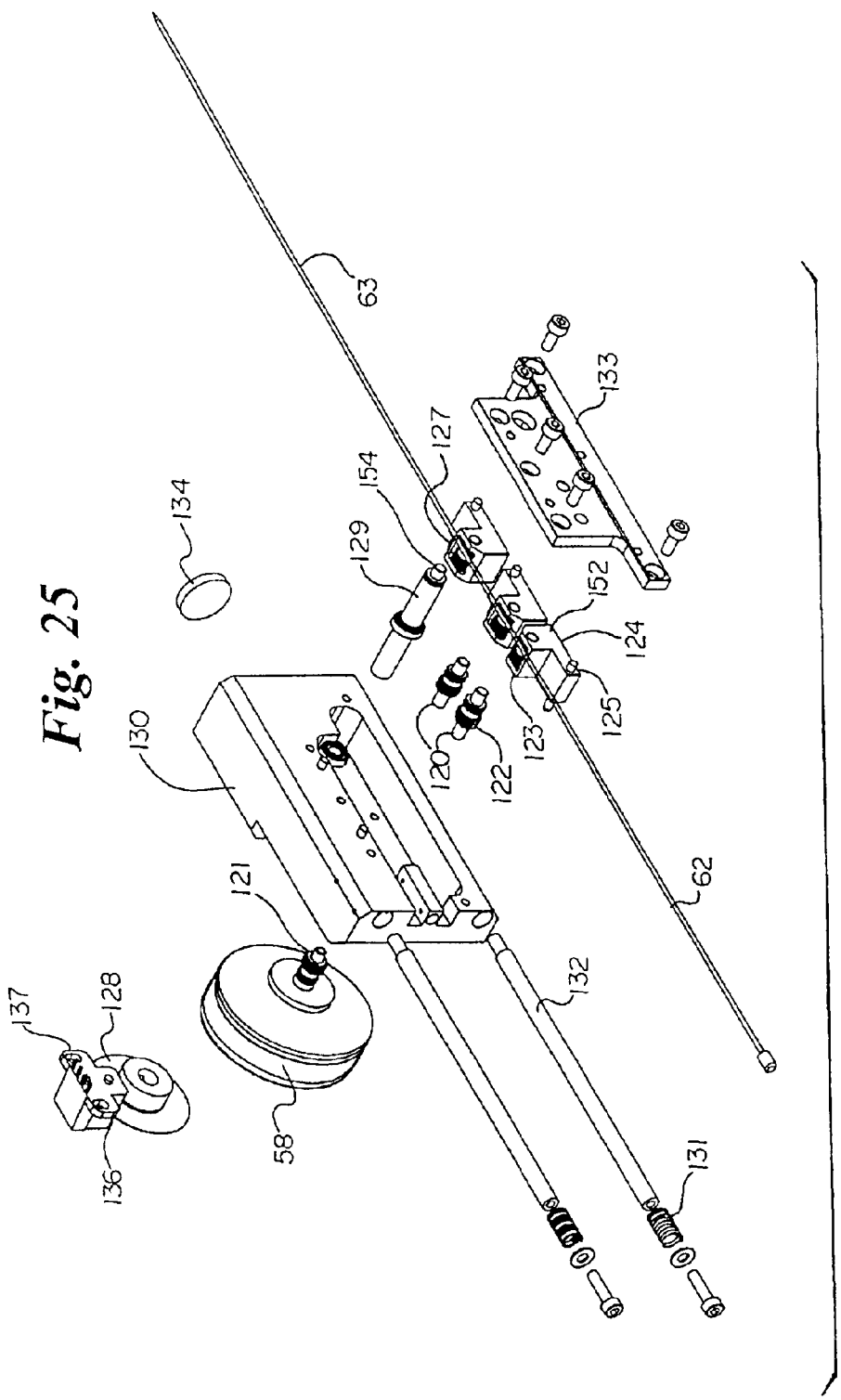
FIG. 25 is an exploded view of the capstan assembly of the cartridge of FIG. 6.
Figure 26:
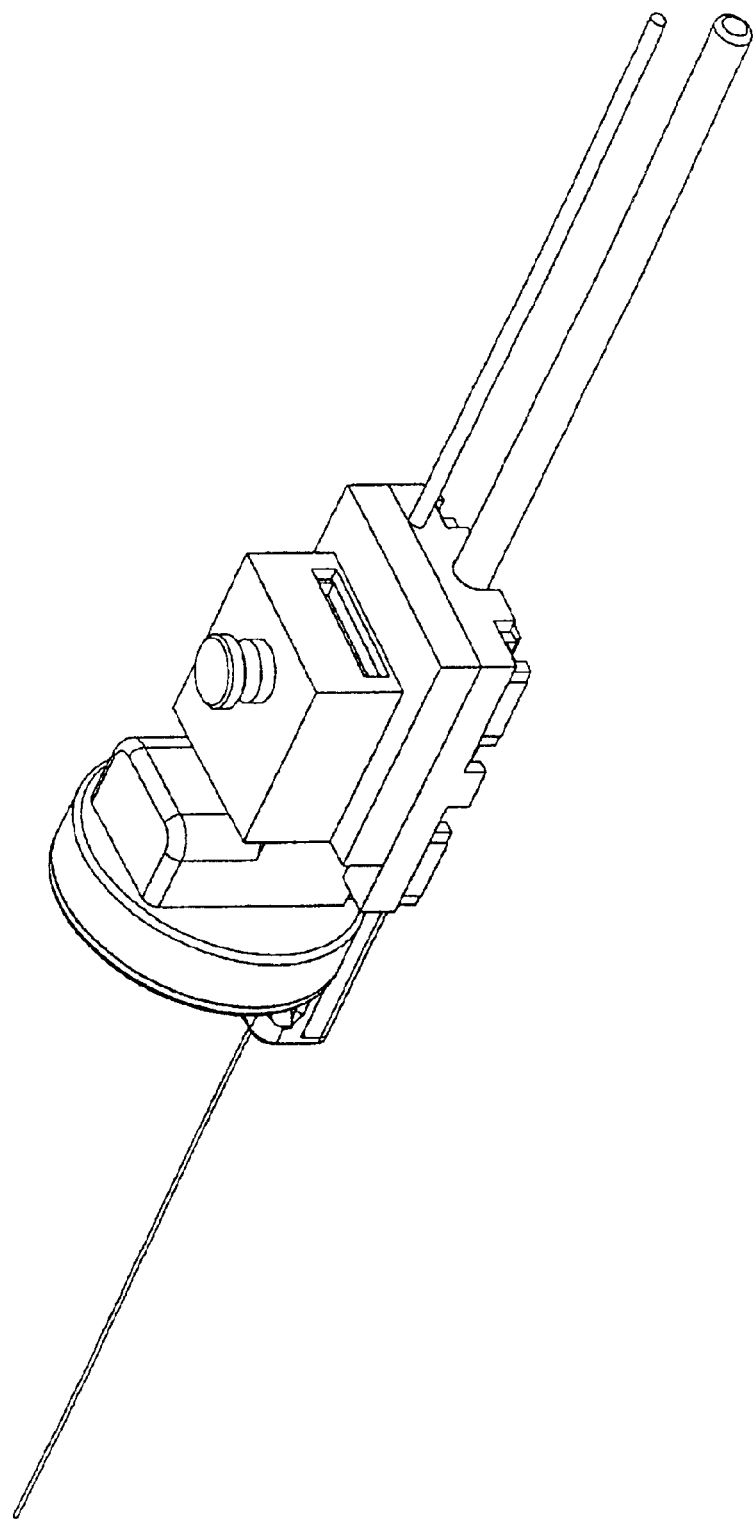
FIG. 26 is a perspective view of a preferred embodiment of the moveable assembly.
Figure 27:
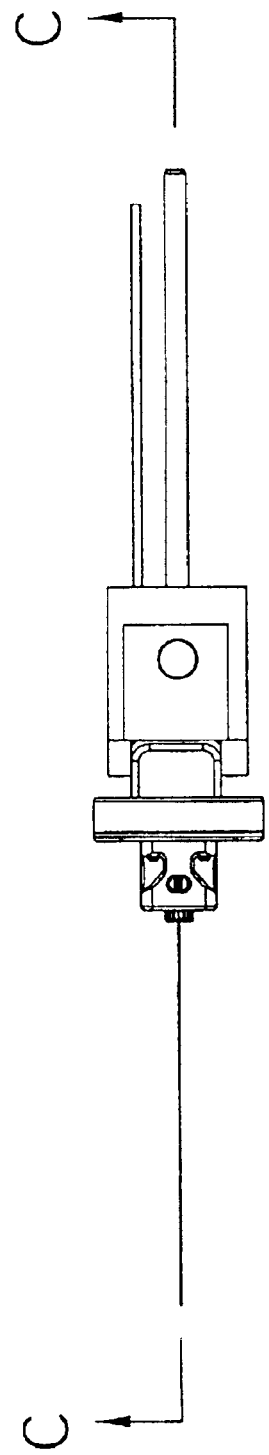
FIGS. 27 and 28 are cross-sectional view of FIG. 26.
Figure 28:
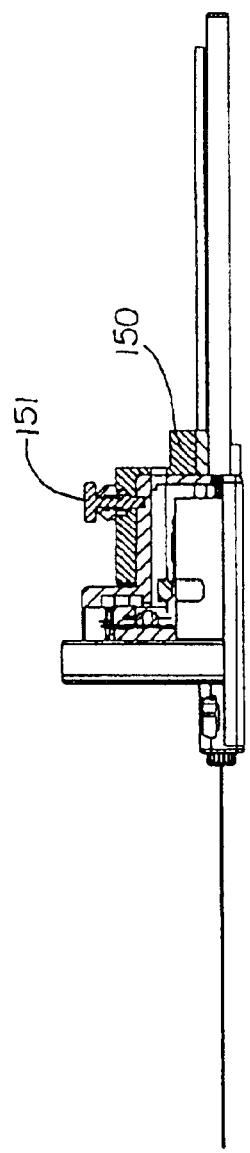

Referring now to FIGS. 6 and 25, a preferred embodiment of the capstan assembly 60 will be described. A pair of capstan drives 120 are preferably positioned above and below the line of travel of trochar needle 62. In this embodiment, a stepper motor 58 drives a drive shaft 121 that is coupled via gears to an upper member 122 of the capstan drives 120. A lower member 123 of the capstan drives 120 is preferably held in a biased pivot arm 124 biased by a spring 125. The pivot arm 124 pivots to allow the trochar needle 62 to enter the capstan assembly 60. Once engaged, the channel guides the trochar needle 62 as it is frictionally held between the upper member 122 and lower member 123 of each capstan drive 120. Each member 122, 123 preferably includes a radial groove 126 in which the trochar needle 62 rides as it is moved. In this embodiment, another capstan 127 is connected to an encoder disc 128 by a pinion 129 for driving the canula 63. This arrangement allows for capstan drives 120 to drive the trochar needle 62 forward and backward with potential slippage in the event that the trochar should encounter excessive resistance. The capstan 127, however, is not being driven and therefore accurately records the movement of trochar needle 62 past this position.

In this embodiment, the capstan drives 120 and 127 are held within a capstan body 130. The capstan body 130 is spring biased by springs 131 at the end of mounting rods 132. A cover plate 133 holds the capstan drives 120 and 127 within the capstan body 130. A force sensor 134 is operably connected to at least the trochar needle 62 and to the needle automated motion control system. The force sensor 134 senses whether the needle assembly 22 encounters resistance that exceeds an expected force associated with piercing tissue when the needle automated motion control system advances the trochar needle 62. When the force sensed by the force sensor 134 exceeds the expected value, the force sensor 134 causes the needle automated motion control system to stop advancing the needle assembly 22 along the insertion axis 20. In a preferred embodiment, the force sensor 134 is a load cell mounted at the front of the capstan assembly 60. The spring biased mounting rods 132 are prebiased to hold the capstan assembly 60 against the load cell 134 at a predetermined pressure. The compliant mount of the capstan assembly 60 provides for a minimum travel distance in the event that the trochar needle 62 encounters resistance that exceeds the force expected for piercing tissue. The compliant mount thereby forms a safety buffer that allows the trochar needle 62 to retract. The force sensor 134 also senses whether the needle assembly 22 has advanced into a non-tissue region. When such an action is sensed, the force sensor 134 no longer registers the prebiased pressure and effectively notifies the user that the needle assembly 22 has advanced into the non-tissue region. Preferably, a travel of up to 3 mm is allowed by the compliant mount of the capstan assembly 60.

A positive travel limit is preferably established using a first optical sensor 136 that is part of the structure of capstan assembly 60 which detects the back of the trochar needle 62 passing through a defined point. A negative travel limit for the line of travel of trochar needle 62 is established by a second optical sensor 137 that doubles as a home reference. Preferably, the travel limits do not disable the second stepper motor 58, but rather send an indication to the automated motion control system 32 that the respective travel limit has been exceeded. Once zeroed in relation to the home reference, the trochar needle 62 is moved forward and into an open chamber 52 in the drum 54. This serves as a loose mechanical lock to prevent the drum 54 from being rotated unintentionally.

The canula 63 preferably includes an annular wiping seal 138 positioned along the insertion axis 20 at a distal end of a staging area 140. The canula 63 also preferably includes a second annular wiping seal 139 positioned along the insertion axis 20 at a proximal end of the staging area 140. In one embodiment as shown in FIG. 2, the needle assembly 22 preferably includes a bellows structure arranged around the canula 63 to collect body fluids and materials when the needle assembly 22 is withdrawn from the patient.

In the preferred embodiment, the implantation station 12 does not include a radiation sensor for safety reasons owing to the high voltage source required for such radiation sensors and the close proximity that such a high voltage source would need to be in relation to the needle assembly 22 that will be inserted into the patient. Accordingly, the preferred embodiment utilizes a modified version of the loading station as described in the parent application to perform an on-site verification of the contents of the cartridge 14. The cartridge 14 is placed in a second cartridge receiving structure in the loading station without the needle assembly 22 attached and a transition tube is used to connect the cartridge 14 with an empty cartridge located in a first cartridge receiving structure in the loading station. The loading station then empties a selected portion of the radioisotope seeds from the cartridge 14 into the empty cartridge and then reloads this selected portion back into the cartridge 14. During this process, the radiation sensor in the loading station can assay the strength of the selected portion of the radioisotope seeds to verify that the radioisotope seeds in the cartridge 14 are the correct seeds to be implanted in the patient. This process could also be utilized to load the cartridge 14 or to alter the contents of the cartridge 14 at the hospital site. In an alternative embodiment, a separate radiation sensor could be incorporated into the implantation station and the cartridge 14 provided with a second aperture through which a separate push rod or trochar, not in electrical contact with the trochar needle 62, could advance the radioisotope seeds past the radiation sensor.

Figure 21:
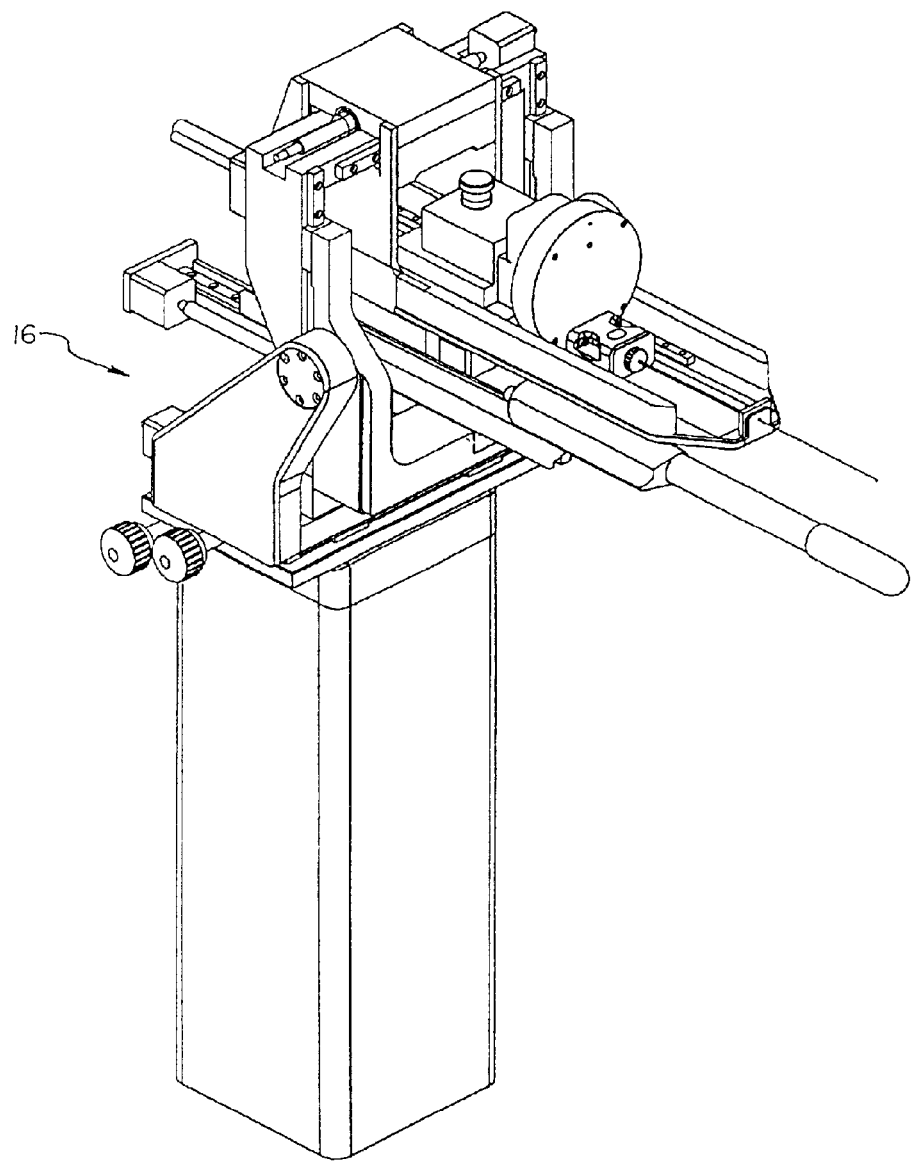
FIGS. 21, 22, and 23 are three different perspective views of a preferred embodiment of the moveable assembly of the present invention.
Figure 22:
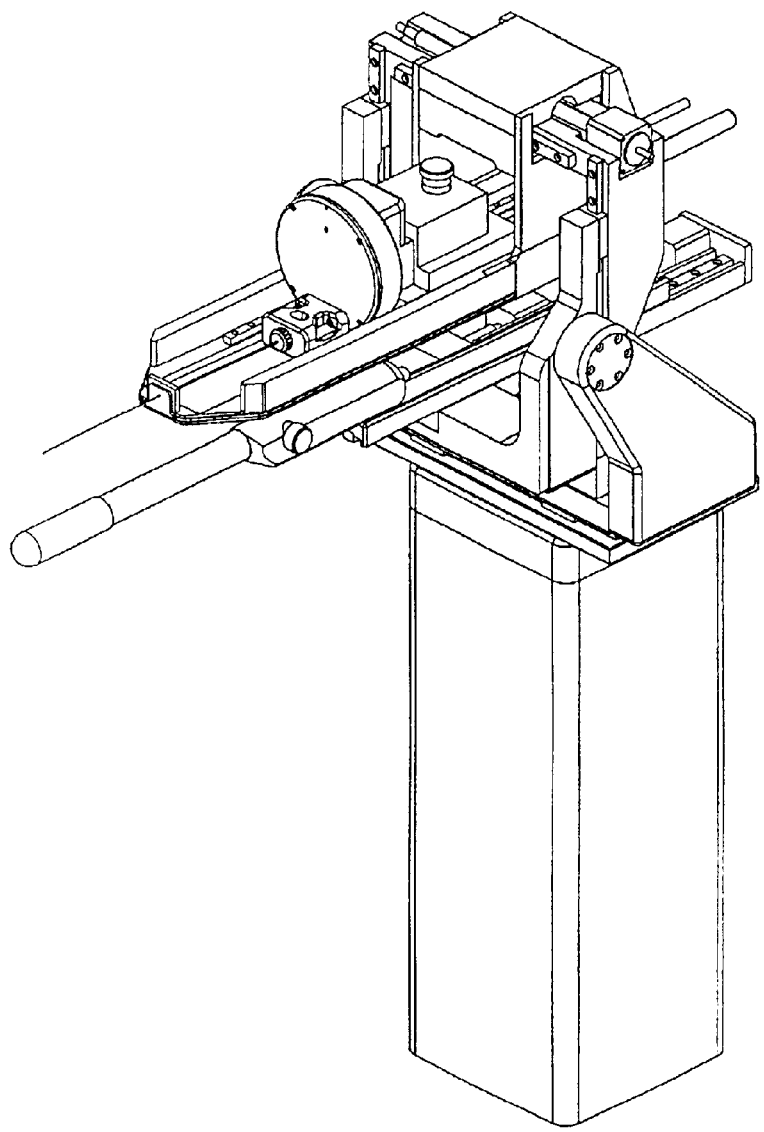
Figure 23:
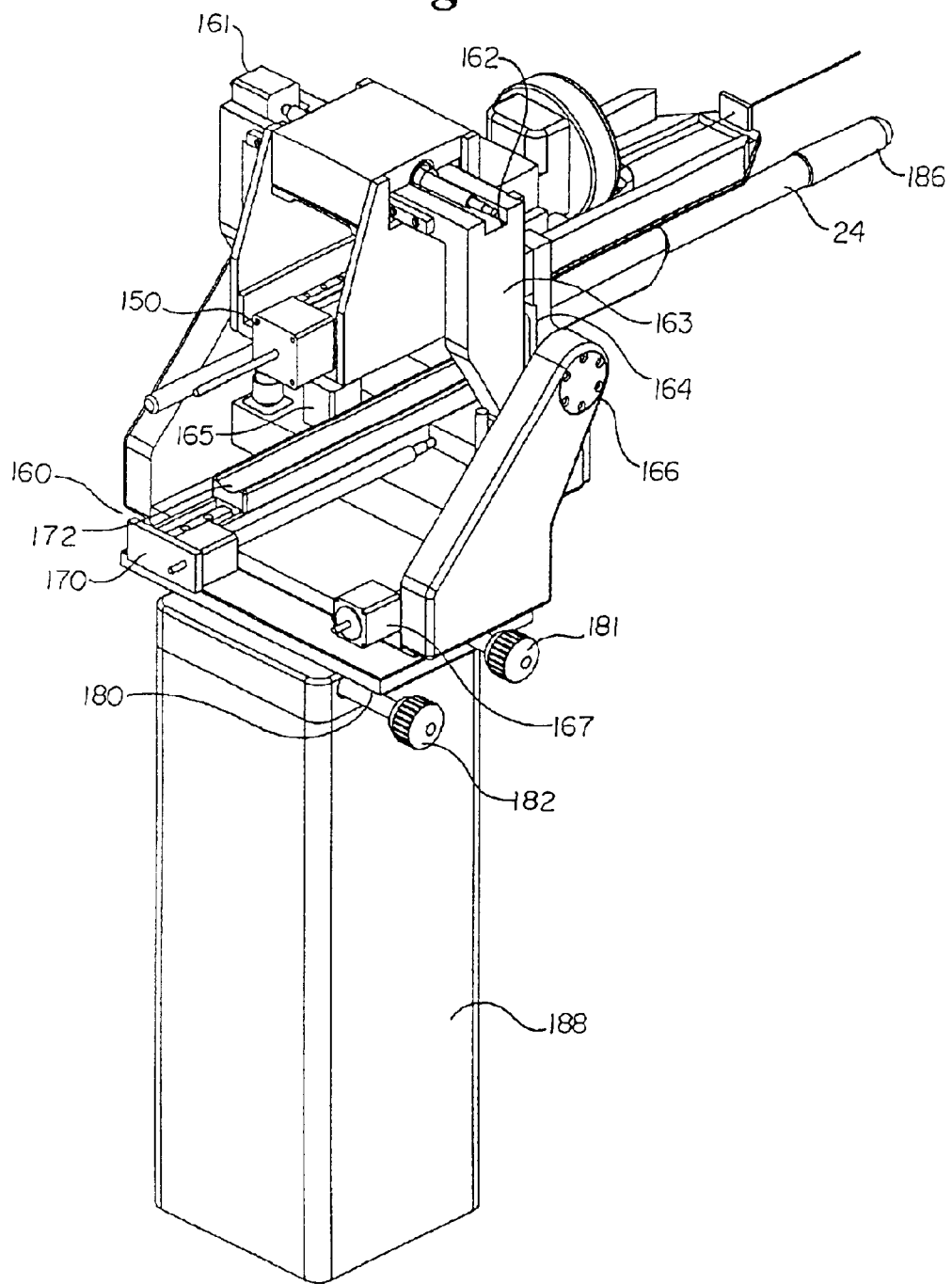
Figure 24:
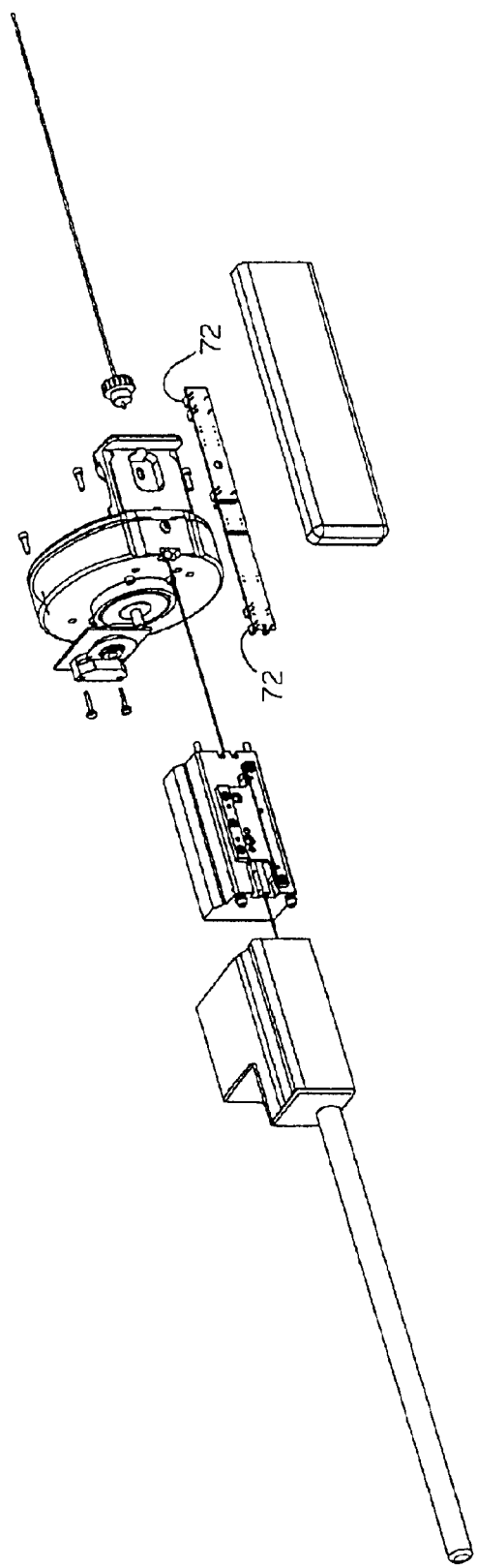
FIG. 24 is an exploded view of the cartridge of FIG. 6.

Referring to FIGS. 21-23, the moveable assembly 16 includes a Z-axis motion system 150 that selectively moves the cartridge receiving structure 18 and the needle assembly 22 along the insertion axis 20. Preferably, the Z-axis motion system 150 is controlled by the automated motion control system 32, which in turn is directed by the computer processor 30, all of which together can be thought of as a Z-axis motion control system. The Z-axis motion system 150 selectively ejects radioisotope seeds from the aperture 50 of the seed cartridge 14 into the needle assembly 22 when the seed cartridge 14 is positioned in the cartridge receiving structure 18. The Z-axis motion system 150 preferably moves the cartridge receiving structure 18 and the needle assembly 22 together to maintain a relative position between the seed cartridge 14 and the needle assembly 22 along the insertion axis 20. Preferably, the seed cartridge 14 and needle assembly 22 have a total travel movement of between 7-8 inches.

As shown in FIG. 25, the Z-axis automated motion control system 150 preferably includes a needle automated motion system 152 that controls the capstan assembly 60 to drive the trochar needle 62 and a canula motion system 154 that controls the canula 63. In the preferred embodiment, the canula motion system 154, the canula 63 is fixed relative to the cartridge 14 and the canula motion system 154 moves the entire cartridge 14. The needle motion system 152 and the canula motion system 154 cooperate to initially move the trochar needle 62 and the canula 63 along the insertion axis 20 by repetitively advancing the trochar needle 62 a distance beyond the canula 63 and then advancing the canula 63 an approximately equivalent distance. The distance the needle motion system 152 advances the trochar needle 62 beyond the canula 63 is preferably between about 0.5 and 2.0 centimeters.

In particular, the needle motion system 152 and the canula motion system 154 cooperate to initially move the trochar needle 62 and the canula 63 along the insertion axis 20 until the needle assembly 22 is inserted a desired depth into the patient. The Z-axis automated motion control system 150 selectively ejects a radioisotope seed 110 and a spacer 114 into the canula 63 as a pair oriented longitudinally along the insertion axis 20 and advances the pair along the insertion axis 20 by pushing the spacer 114 with the trochar needle 62. To load the pair, the needle motion system 152 preferably withdraws the trochar needle 62 once the canula 63 is positioned as desired to accept a plurality of pairs each consisting of a radioisotope seed and a spacer in the canula 63. Each pair is moved along the insertion axis 20 to a staging area in the canula 63 proximal to the distal end of the canula 63 until all of the pairs for a current location of the canula 63 are in the staging area after which the needle motion system 152 advances all of the pairs along the insertion axis 20 to the distal end of the canula 63. The canula motion system 154 withdraws the canula 63 once all the radioisotope seeds are positioned. The needle motion system 152 keeps the trochar needle 62 in place until the canula 63 is withdrawn. In a preferred embodiment, there are three optical sensors 72 (FIG. 10) that sense the position of the trochar needle 62 as fully withdrawn, indexed into the drum 54 or just extended (approximately 3 mm) past the drum 54 into the staging area 140.

The moveable assembly 16 also preferably includes an X-Y axis motion system 160 that selectively moves at least the cartridge receiving structure 18 and the needle assembly 22 in the base plane 21 that is substantially perpendicular to the insertion axis 20. The X-Y axis motion control system 160 preferably moves the cartridge receiving structure 18 and the needle assembly 22 together to maintain a relative position between the cartridge receiving structure 18 and the needle assembly 22 in the base plane 21. The X-Y axis motion control system 160 includes an X-axis stepper motor 161 mounted on a top rail 162 on a U-shaped hanger 163 from which the cartridge receiving structure 18 depends. The X-axis stepper motor 161 moves the hanger 163 left and right relative to the patient. The base arms of the hanger 163 include channel structures 164 that are connected to the drive mechanism of a Y-axis stepper motor 165 that can move the hanger structure 163 up and down relative to the patient. Preferably, a single motor, two drive screw arrangement is used with a pair of corresponding drive rails to prevent any offset in movement from one side to the other of the hanger structure 163. In a preferred embodiment, the drive rails are split drive rails that move apart as the hanger structure 163 is lowered to minimize the length of the corresponding base plate. Preferably, a pair or rotatable bearings 166 mount the hanger structure 163 in such a way that a tilt stepper motor 167 can tilt the orientation of the hanger structure 163. This allows the angle of the moveable assembly to be adjusted. In a preferred embodiment, the tilt stepper motor can provide a range of tilt of 10 degrees above horizontal to about 45 degrees below horizontal.

The moveable assembly 16 also preferably includes a manual rotational motion arrangement 180 connected to the moveable assembly 16. The rotational arrangement 180 pivots the moveable assembly 16 about a vertical axis relative to the base 15. Preferably, a rotation of between 5–10 degrees on each side of the center axis is allowed to enable the moveable assembly 16 to be properly positioned with respect to the patient. A knob 181 tightens or loosens the rotational arrangement 180 to turn the moveable assembly 16. A manual lateral adjustment is also provided to allow for manual adjustment from side to side of the moveable assembly 16 relative to the patient. Again, a knob 182 tightens or loosens the manual lateral adjustment to allow the moveable assembly to slide laterally.

In a preferred embodiment, the computer processor 30 adjusts the base plane 21 in response to a user directive and all subsequent radioisotope seeds placed by the implantation system 10 are placed at a depth determined from the adjusted base plane 21. Alternatively, computer processor 30 can monitor a position of an organ being treated in the brachytherapy procedure and selectively adjusts a base plane 21 position of the Z-axis automated motion control system 150 in response to movement in the position of the organ during the brachytherapy procedure.

The position of the organ is preferably monitored with an ultrasound probe 24. The position of the ultrasound probe 24 is controlled by a second Z-axis automated motion control system 170 such as a stepper motor of linear screw drive coupled to a motion controller such as motion controller 32. The second Z-axis automated motion control system 170 selectively moves the ultrasound probe 24 along a probe axis 19 that is generally parallel to the insertion axis 20. The computer processor 30 preferably executes a dosimeter software routine that develops a dose plan for the patient based on images provided by the ultrasound probe 24. The ultrasound probe 24 is preferably removably mounted within a carrier structure 172 defined on the moveable assembly 16. Preferably, the carrier structure 172 includes a mechanism that allows for rotation of the ultrasound probe 24 relative to the probe axis 19 and selectively locks the ultrasound probe 24 in a desired rotation in response to a command from the computer processor 30. Preferably, the ultrasound probe 24 has a total travel distance similar to the seed cartridge 14 of about 7–8 inches.

The ultrasound probe 24 further includes an outer rigid sheath 186 coaxial with the ultrasound probe 24. The Z-axis automated motion control system 170 initially positions the outer sheath 186 and the ultrasound probe 24 in the patient. The Z-axis automated motion control system 170 also moves the ultrasound probe 24 along the probe axis 19 and within the sheath 186 to generate ultrasound images along the probe axis 19. The purposes of the sheath 186 is to stabilize the prostate gland which tends to ride on top of the ultrasound probe 24 as the ultrasound probe 24 is inserted in the patient's rectum. If the ultrasound is withdrawn or moved during the procedure, there is a tendency for the prostate gland to tip or slid off the end of the ultrasound probe, thereby affecting the subsequent placement and location of radioisotope seeds. By utilizing a relatively rigid, yet thin ultrasound sheath 186, the preferred embodiment of the present invention solves this problem in that the prostate gland remains in a constant position relative to the ultrasound sheath 186, regardless of where the ultrasound probe 24 is moved within the sheath 186.

The computer processor 30 preferably captures and stores at least one image from the ultrasound probe 24 each time the needle assembly 22 is located at a different position in the plane 21 perpendicular to the insertion axis 20. The computer processor 30 also preferably captures and stores at least one image from the ultrasound probe 24 when the needle assembly 22 is moved forward along the insertion axis 20 to a distal most location where radioisotope seeds will be placed.

The computer processor 30 includes an autocalibration routine that calibrates an XYZ relationship of the ultrasound probe 24 to the needle assembly 22 each time a different ultrasound probe is used with the automated implantation system 10. Preferably, the tilt mechanism allows the moveable assembly 16 to be tilted downward at an angle of approximately 45 degrees so as to allow the ultrasound probe 24 to be advanced into a container of water for example to test and calibrate the new ultrasound probe.

Figure 7:
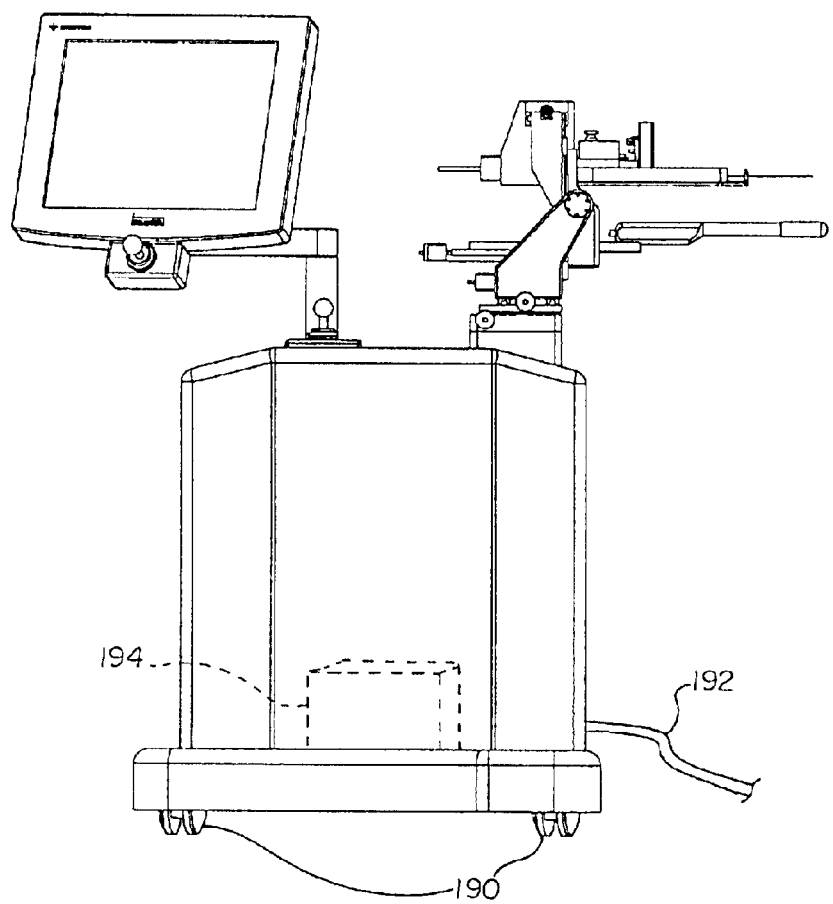
FIGS. 7, 8, and 9 are front, top, and end plane views of the automated implantation station of FIG. 1, respectively.
Figure 8:
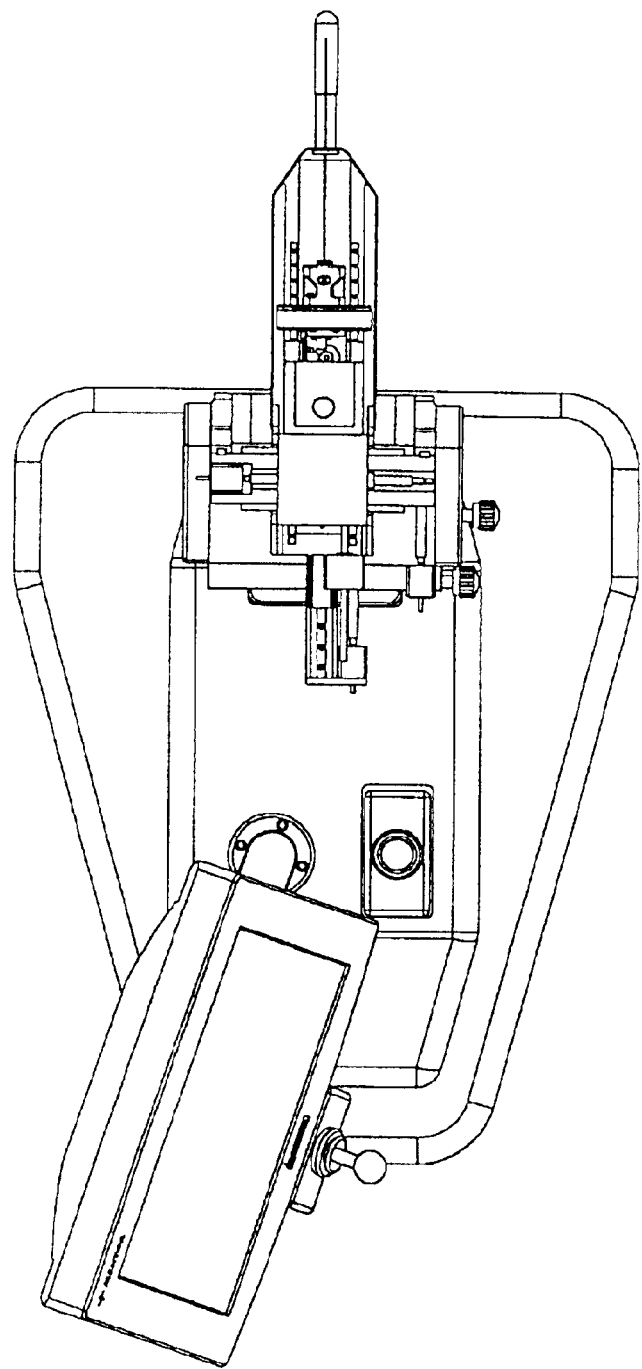
Figure 9:
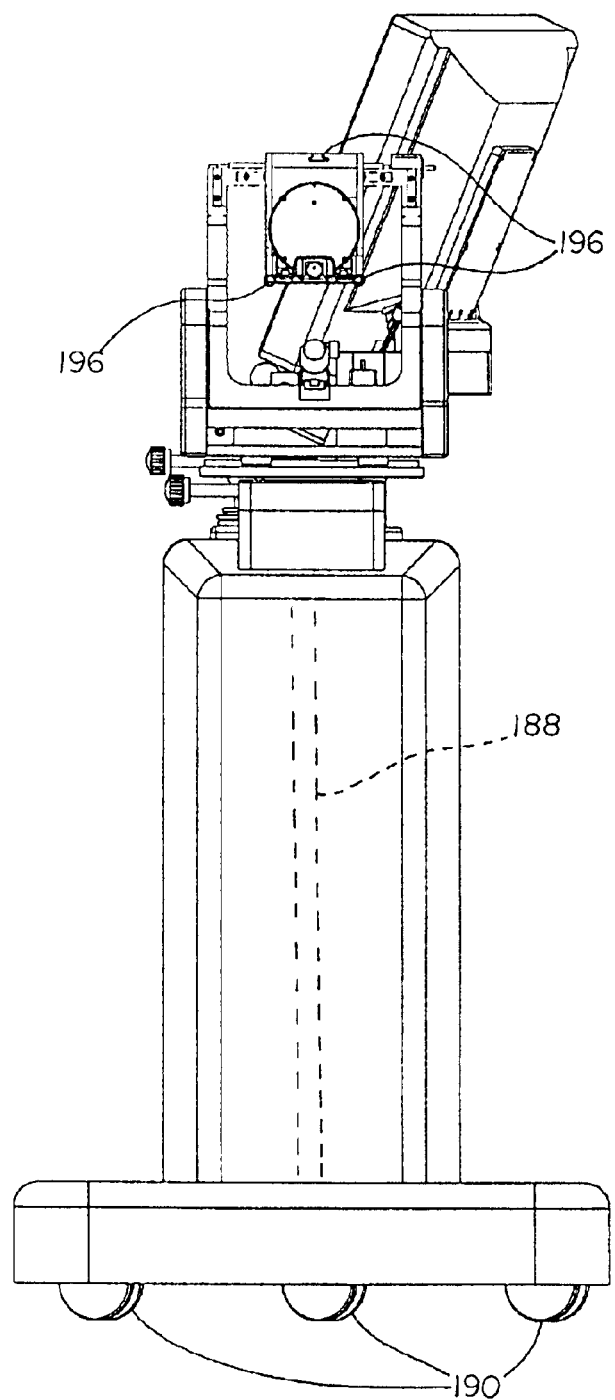
Figure 10:
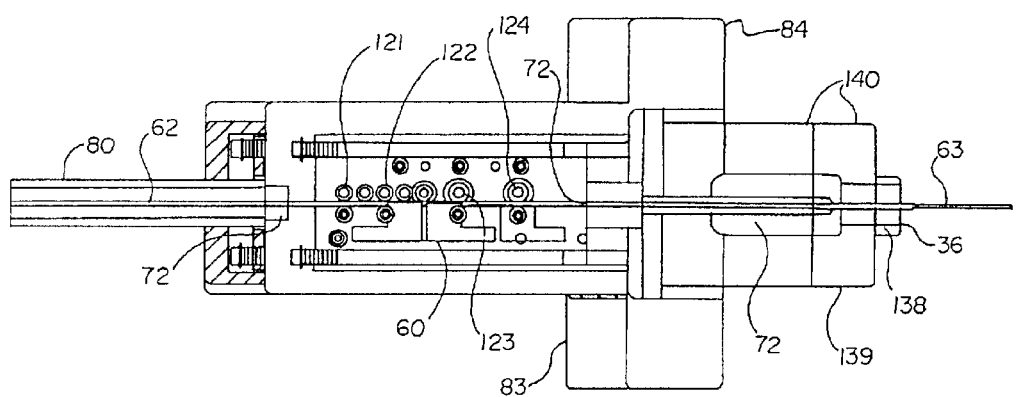
FIGS. 10 and 11 are sectional views of the replaceable cartridge of FIG. 6.
Figure 11:
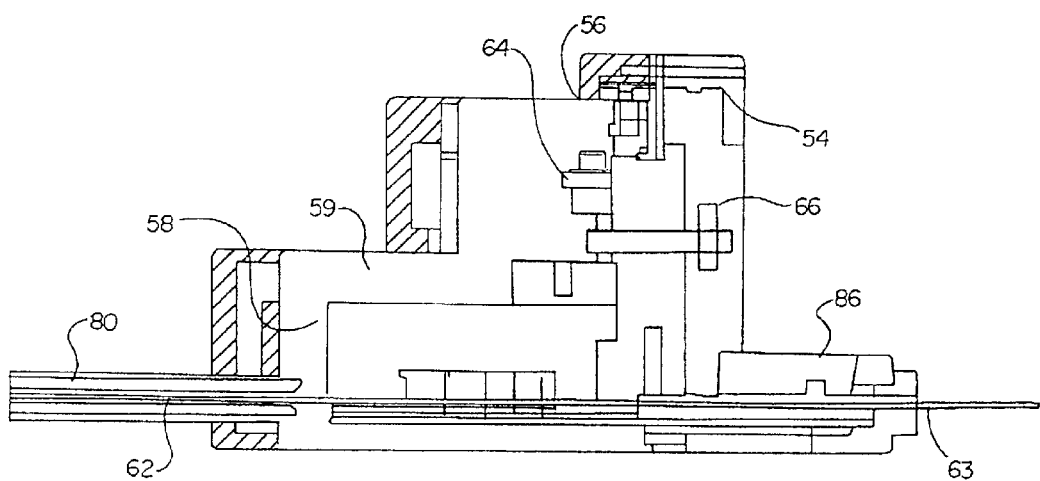

The stand 17 includes a gross vertical adjustment mechanism 188. The gross vertical adjustment mechanism 188 adjusts a vertical height of the moveable assembly 16 relative to the base. Preferably, an up and down travel of up to 12 inches is provided The gross vertical adjustment mechanism 188 is preferably motorized. The base 15 also preferably includes a set of retractable wheels 190 (FIGS. 7 and 9) that allow the implantation station 12 to be moved when the wheels 190 are extended and provide a stable position for the implantation station 12 when the wheels 190 are retracted. The automated implantation system 10 preferably includes alternative power sources. A primary power source connection 192 plugs into an external outlet and a secondary power source is supplied from a battery 194 housed in the stand 17. The secondary power source is configured to replace the primary power source in the event that the primary power source 192 is unplugged from the external outlet.

In one embodiment, a set of LEDs 196 are provided on the moveable assembly that are targeted to project a beam of light a predetermined distance in front of the guide bushing 31 at a common triangulated point, for example. The intersection of these beams of light define a target point that is a defined distance in front of the guide bushing 31 along the insertion axis 20 for positioning the location of the insertion axis 20 relative to the patient.

Figure 12:
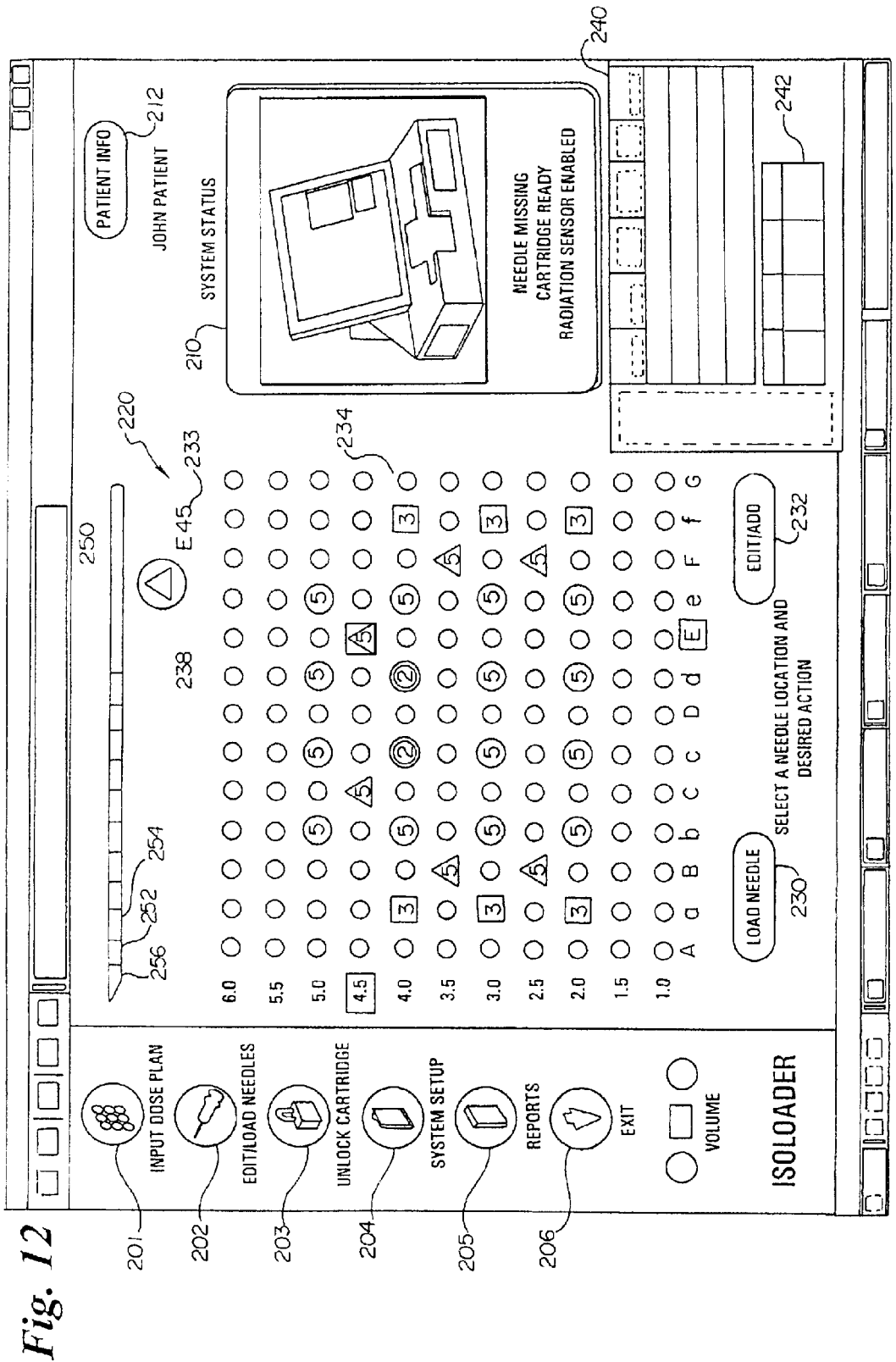
FIGS. 12 and 13 are graphic depictions of a preferred embodiment of a user interface screen of a display of the automated system of FIG. 1.
Figure 13:
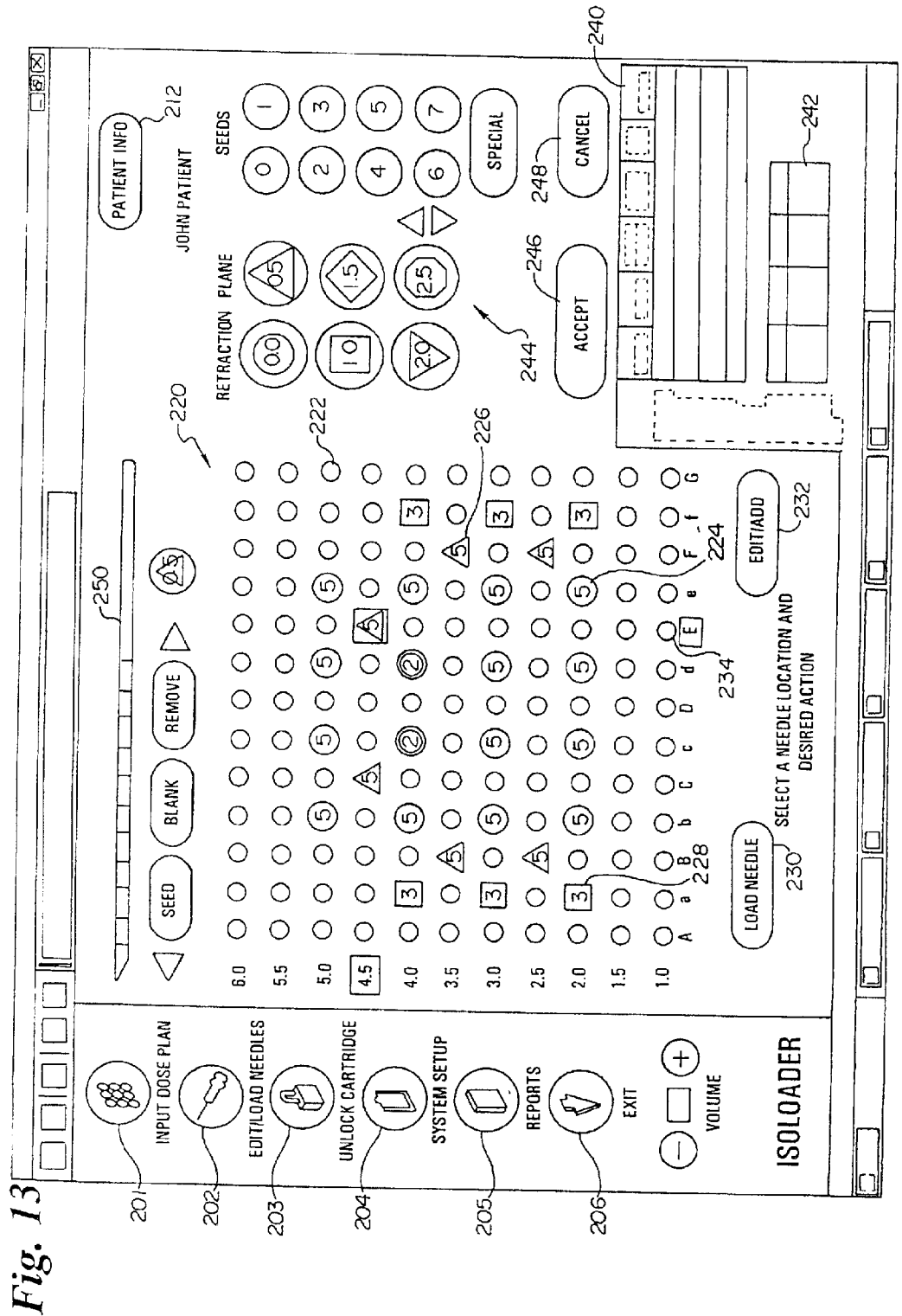

Referring now to FIGS. 12 and 13, a preferred embodiment of the user interface 200 as presented on display 40 (FIG. 1) will now be described. Preferably, the display 40 is a touch screen display and the computer processor 30 utilizes a Windows® NT operating system with a Radisys® In Time environment. To a user, however, the user interface 200 preferably appears as a dedicated virtual machine having a single primary touch-screen user screen as shown in FIG. 12. Although the preferred embodiment of the present invention will be described in connection with a touch-screen user interface 200, it will be recognized that various other user interfaces, such as conventional video displays, LCD displays or specialized displays may also be used with the present invention. In addition, it would be possible to provide for an audio-controlled user interface coupled with an optional display screen to allow for voice-activated control of the loading process.

In the preferred embodiment of user interface 200, a series of dedicated touch-activated buttons 201 to 206 are positioned to always remain visible on the left side of the display. The user interface 200 is preferably designed to provide a very flat icon-based menu structure with minimal overlay windows where all of the functions controlled by a user are accessible though each touch screen inputs. A virtual keyboard may be selected to enter alphanumeric data. Alternatively, a mouse and keyboard may be connected to the computer processor 30 to enter such data. Another equivalent input device is a joystick or game port pad or equivalent pointing/directional input device. Preferably, each of the buttons 201–206 has an icon on the top half of the button and a corresponding text message on the bottom half of the button.

A status icon 210 is preferably displayed along the left of user interface 200 to display status messages such as Cartridge Detected, Reading Inventory, Running Diagnostics, Verifying Sensors, Cartridge Ready, Printing and the like. Once a cartridge 14 has been successfully loaded and locked into the cartridge receiving structure 18, at least the patient name information from the EEPROM 79 of that cartridge 14 is displayed in the top left corner of the user interface 200. Additional patient information can be accessed through button 212. In a preferred embodiment, the system status area 210 is also used as a multi-media help screen that can display information about using the system 10, as well as general information about the particular brachytherapy procedure to be performed. A volume control 216 is provided to conveniently control the audio volume of multi-media information displayed on the status area 210.

The primary display in the main part of the user display 200 is the loading pattern grid 220 that replicates an interactive grid of how the radioisotope seeds are to be implanted in a format that is similar to the paper format currently used for prostate cancer brachytherapy procedures. In this format, the numbers along the left side of grid 220 represent the height in centimeters and the letters represent the width in 0.5 centimeter increments (1.0 centimeters between capital letters) of the locations where the radioisotope seeds are to be inserted from a reference base axis that would be located at 0.0. The open circle icons 222 at the intersection of each of these coordinates represents a chamber in an implant grid that is used to implant the series of implant needles 230.

Each of the icons 224, 226, 228 in the center of grid 220 represents a row of radioisotope seeds to be implanted with the number in the center of the icons 224, 226, 228 indicating the number of radioisotope seeds 110 that are planned for that location. The circle icons 224 are for needles in which the seeds 110 are spaced at regular intervals using full-length spacers 112. The triangle icons 226 are for needles in which the seeds 110 are spaced at regular intervals, but are offset or staggered by using at least one partial-length spacer 114. The square icons 228 represent those locations in which the seeds 110 are not spaced at regular intervals due to the staggering of partial length spacers 114 and full-length spacers 112.

The grid 220 is active, as shown in FIG. 13, when the Edit/Add Needles button 232 is activated. The currently active location is indicated by the message 233 at the upper right corner of the grid 220 and by the intersecting lines 234 that highlight that coordinate in the grid. A user selects a different currently active needle location by pointing to that location. In one embodiment, the status of each of the icons 224, 226 and 228 are conveniently shown in the colors as indicated in the scoreboard area 240. The scoreboard area 240 is dynamically updated by the computer 30 to reflect the planned, loaded, not yet loaded, cartridge inventory, extras and discards that the user has available or has used. The Edit control area 244 allows a user to select retraction plane depths and number of seeds for the active needle location. Once the desired configuration is selected, the user accepts the configuration for the active needle location by entering button 246. Alternatively, the information for this location can be discarded by selecting the cancel button 248.

Once a user activates the Implant Needle button 230, as shown in FIG. 12, the X-Y automated motion control system 160 position the insertion axis 20 at the location indicated for the selected icon. Once the moveable assembly 16 is in position at the proper insertion axis 20, the needle automated motion control system 152 and the canula automated motion control system 154 repetitively advance the needle assembly 62 a distance beyond the canula 63 along the insertion axis 20 and then advance the canula 63 that same distance until the canula 63 is positioned at a desired depth relative to the base plane. The needle automated motion control system then withdraws the trochar needle 62 once the canula 63 is positioned at the desired depth to accept a radioisotope seed. Finally, the needle automated motion control system advances the trochar needle 62 to position the radioisotope seed in the canula 63 at the desired position.

As a location is implanted, position indicators 252 and 254 in the needle icon 250 represent locations in the implant needle in which radioisotopes 110 and spacers 112, 114 may be loaded. As the implanting process progresses, seed icons 252 and spacer icons 254 are displayed in the respective position indicators where those items are positioned in the needle assembly 22.

The Input Dose Plan button 201 allows a user to input a predetermined dose plan. Two input options are provided, a Manual Input option and a Load File option. In the Manual Input option, the grid 220 is displayed with no predetermined dose plan overlayed. In this mode, the user would select a desired location and then use the Edit/Load Needle button 202 to indicate how the needle assembly should be filed corresponding to that location. This process would then be repeated for each location to be implanted via this manual option. In the Load File option, a pop-up window is displayed showing the default dose plan that was used to generate the configuration of contents of the particular cartridge 14. In a preferred embodiment, a compact disc (CD) is delivered along with the cartridge 14 to the hospital where the procedure is to be performed and the default dose plan is contained on this CD and is read by the CD player 38.

In another embodiment, a compressed version of the default dose plan is stored on the EEPROM 79 in the cartridge 14. If the automated system 10 was used during the generation of the dose plan at an initial planning visit or at the time of the procedure, then the dose plan would be stored on the hard drive 34. Alternatively, the default dose plan could be stored on a floppy disc and read by the floppy disc drive 36 or could even be stored on a remote location and accessed by an external interface, such as by an encoded transmission over the Internet or over a private dial-up network. If the user desires to override the default dose plan and select another dose plan, the pop-up window would allow the user to search the various drives accessible by the automated station to locate an appropriate dose plan file. Preferably, the default dose plan is stored in a proprietary text file format adapted for use by the software running on the computer processor 30.

Alternatively, the computer processor 30 could translate the output files of any of a number of dose planning software packages to the proprietary text file format as part of the process of loading the dose plan. Once an appropriate file has been selected, the user can load the selected file as the dose plan and the details of that dose plan are then displayed on the user interface 200. Alternatively, the computer processor 30 could be provided with the dosimetry software package and a user could develop the dose plan directly on the computer processor 30 either prior to the procedure or during the procedure. For example, the dose plan could be modified as the procedure progresses in response to needles that have been loaded. In this embodiment, a common file structure could be shared between the dosimetry software and the control software running on the computer processor 30 for controlling implanting of the radioisotope seeds.

The Unlock Cartridge button 203 is used to instruct the automated system to initiate the process of preparing for the cartridge 14 to be removed from the cartridge receiving structure 18. Various checks are performed by the computer processor 30 to insure that certain tasks are completed. These tasks include confirmation that no implant needles are in the cartridge, a verification that the current inventory of the seeds 110 in the drum 54 is stored in EEPROM 79, a homing function for the trochar needle 62 into an empty chamber 52 in drum 54 to lock the drum 54 into position. After these tasks are completed, power would be shut off to the cartridge 14 and the solenoid 29 is deactivated to unlock the cartridge 14. A pop-up message is displayed to the user instructing them to manually remove the cartridge 14 from the cartridge receiving structure 18 and providing for an option to cancel this operation. Preferably, a countdown timer is shown during which time the user would be able to manually remove the cartridge 14 and after which the solenoid 29 would be engaged again to relock the cartridge 14 in place. The contact on the electrical connector 28 is monitored to confirm that the cartridge 14 has been removed and the pop-up windows are closed once the cartridge 14 has been removed.

The System Setting button 204 allows the user to view and edit various parameters of the automated system 10, including motion control parameters and display preferences.

The Reports button 205 allows the user to print out certain predetermined reports for the automated system 10, including a dose plan report, a calibration report, a case summary and a system diagnostic report. These reports may be printed directly over the external connections for computer processor 30, may be stored to a file for later printing or review. The user may be provided with certain formatting preferences and printing options to customize certain details of the presentation of these reports.

The Exit button 206 allows the user to exit or switch from the implantation application software back to the operating system software running on the computer processor 30. This button 206 can either be conditioned on a proper shutting down of the automated system 10, including removal of the cartridge 14, or it can allow for an option to switch to another application that could be running on computer processor 30. In one embodiment of the present invention, the computer processor 30 is provided with dose planning software that would be used by the physician to create the predetermined dose plan that is to be used by the needle loading application software.

In another embodiment, the computer processor 30 is provided with dose planning software and with image management software that can capture ultrasound images from the rectal ultrasound probe 24. In this embodiment, the motherboard of the computer processor 30 is provided with a frame-grabber daughter board 33 (FIG. 1) that interfaces with the ultrasound probe 24 to obtain frame-by-frame image of the prostate gland as the probe is advanced. Preferably, a linear stepper motor is coupled to the probe 24 and to the automated motion control system 32 to allow the image management software to control the movement of the probe. In this way, precise control of the frame-by-frame images used for the volume study can be obtained and the dose plan generated as a result of the volume study can be correlated back to the frame-by-frame images.

Preferably, the probe 24 is operated in a similar manner at the time of the brachytherapy procedure and the frame-by-frame images of the volume study can be compared with the current images of the prostate gland. A matching or registration of these two different sets of images can be done manually or with the assistance of the computer processor 30. Once the matching is complete, the dose planning software can compare any changes in the volume or positioning of the prostate gland and update the recommended dose plan accordingly. In this embodiment, as in the preferred embodiment, the number and combination of radioisotope seeds and spacers preloaded into the cartridge 14 can be increased by a given percentage over the minimum number required by the predetermined dose plan to allow for changes to the dose plan as a result of changes to the volume and position of the prostate gland that may occur between the time of the volume study and the time of the brachytherapy procedure. In this embodiment, the physician would utilize the display 40 of the automated system as the display for conducting the volume study and monitoring the brachytherapy procedure, as well as for controlling the automatic loading of the implant needles.

For a more detailed description of the operation of the user interface, reference is made to the co-pending application entitled "User Interface for a Radioisotope System" previously referenced.

Figure 14:
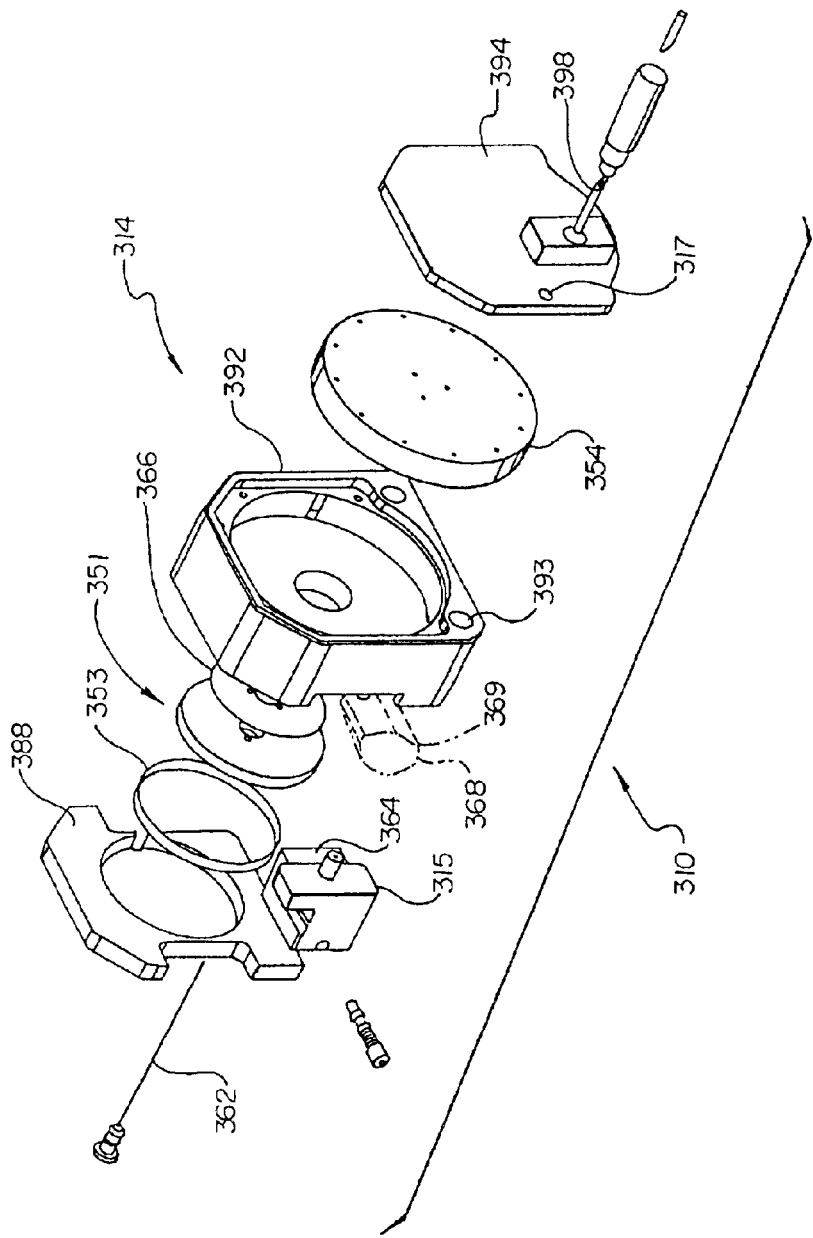
FIG. 14 is a perspective view of another embodiment of the automated system of the present invention having a replaceable cartridge that does not include the stepper motors.
Figure 15:
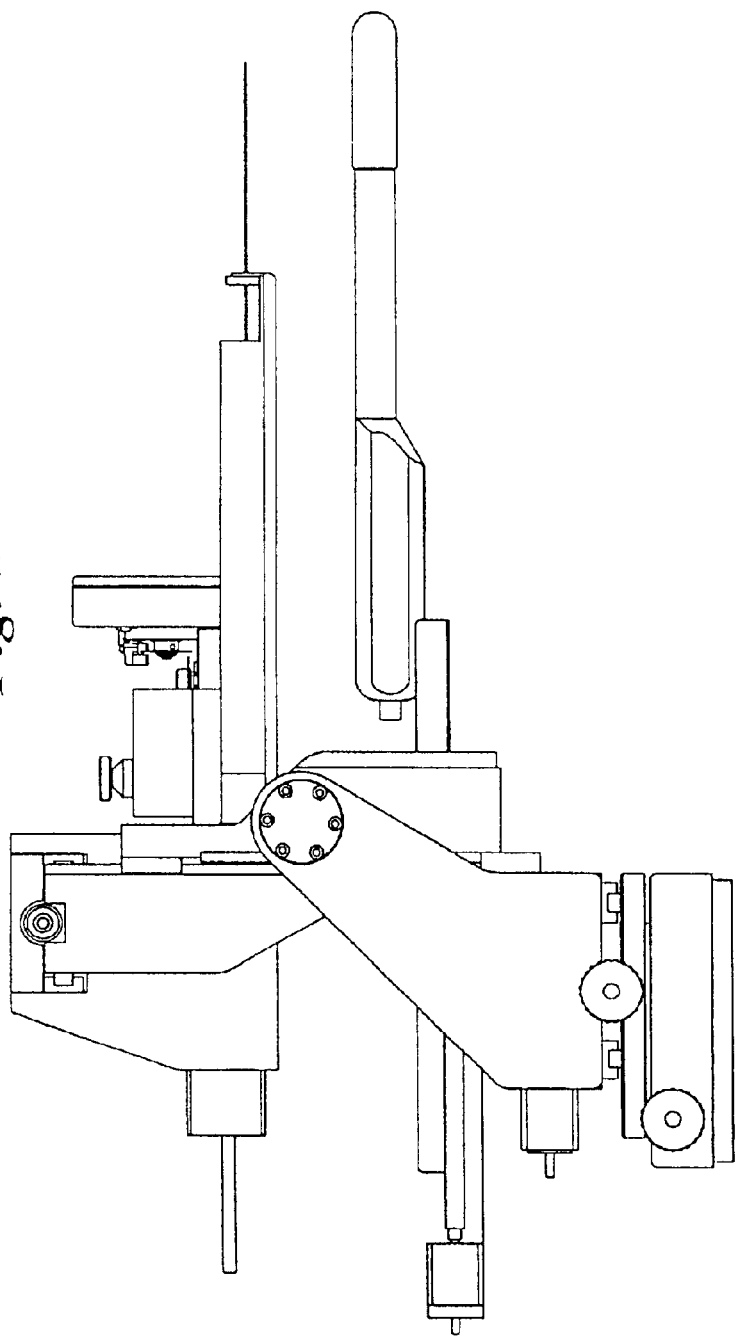
FIGS. 15, 16, and 17 are front, top, and end plane views of the moveable assembly of FIG. 4, respectively.
Figure 16:
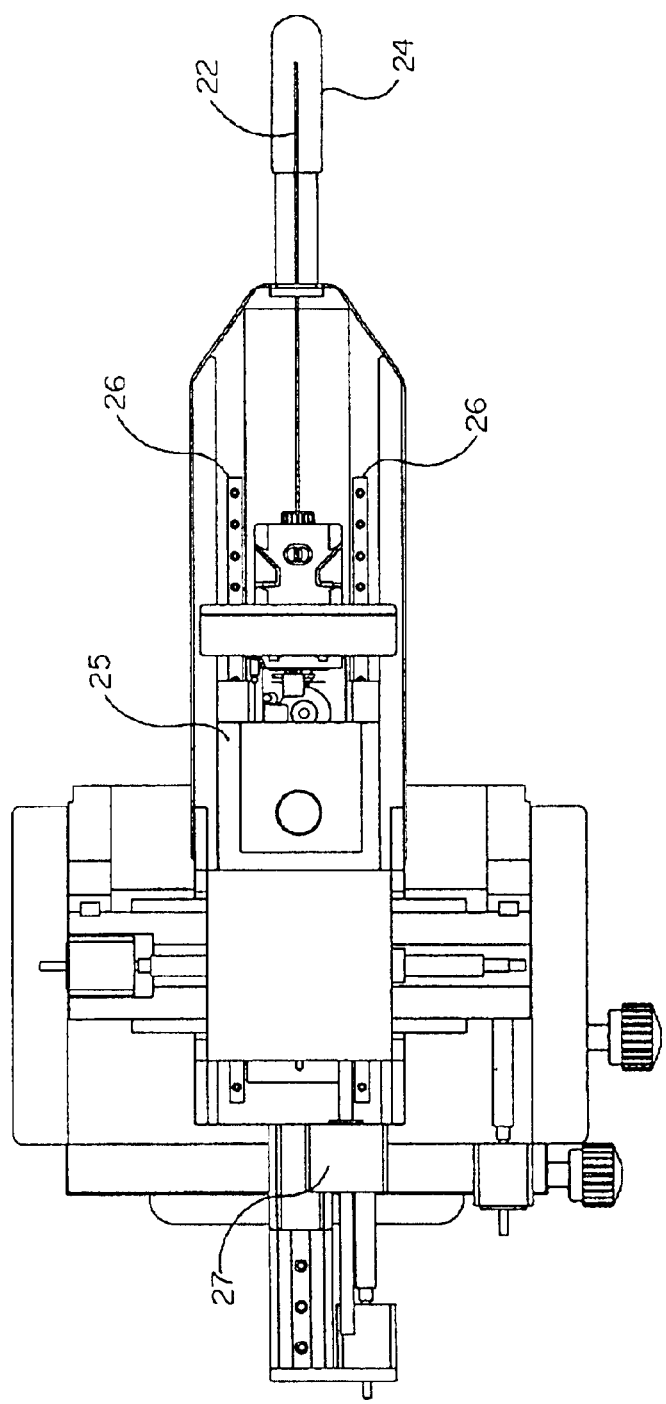

Referring now to FIG. 14, an alternate embodiment of an automated system 310 for loading low dose radioisotope seeds into a plurality of implant needles is comprised of a loading station 12 into which a replaceable cartridge 314 may be positioned. It will be understood that the description of corresponding items in the automated system 310 is similar to the preferred embodiment of the automated system 10 unless otherwise noted. The cartridge 314 does not have any internal stepper motors, but rather interfaces a drive motor (not shown) in the loading station with a drive wheel 351 in the rotatable drum 354. The cartridge 314 is held in place by a position registration mechanism 317 that comprises a ball and detent mechanism with the cartridge having at least one detent defined on an outer surface and the loading station 12 having a cam driven ball mechanism which selectively seats at least one ball in the at least one detent to properly register the position the cartridge 314 within the cartridge receiving structure 318.

An external push rod 362 is carried by a guide rail (not shown) and is driven by a linear actuator (not shown) that is contained in the loading station 12, rather than in the cartridge 314. When the cartridge 314 is in position in the cartridge receiving structure 18, a first drive wheel 351 preferably having a rubber ring 353 and a position encoder 366 in the cartridge 314 are operably engaged by a second drive wheel (not shown) and a position sensor 364 in the loading station 12 to drive and sense the position of the rotatable drum 354 in the cartridge 314.

A position registration mechanism 317 preferably positions the cartridge within the cartridge receiving structure within the tolerance of +/-0.010 inches. Preferably, the position registration mechanism 317 comprises a ball and detent mechanism with cartridge 314 having at least one detent defined on our surface and loading station 12 having a cam driven ball mechanism that selectively seats at least one ball in the least one detent to properly register the position of the cartridge 314 within the cartridge receiving structure 18. The loading station also includes at least one guide rail having a push rod 362 connected to a linear actuator that is controlled by the automated motion control system 310 to selectively eject the radioisotope seeds and spacers from the periphery of the rotatable drum 354 of the cartridge 314.

In this embodiment, the encoder disc 366 for the rotatable drum 354 is part of the cartridge 314, but the encoder circuitry and position sensor 364 for the rotatable drum 354 and the encoder disc 366 and encoder circuitry 368 for the linear actuator 360 are part of the loading station 12. An EEPROM 339 that functions in a manner similar to the EEPROM 79 is part of the cartridge 314, although the design and interface of this EEPROM 339 are configured such that it is easily removed from the cartridge 314 or is encased so as to allow the cartridge 314 to be sterilized without the need to disassemble parts of the cartridge 314. Thus, while there are more critical mechanical tolerances that must be maintained in this embodiment, such as the interface between the optical encoder disc 366 and the position sensor 364, there are fewer electrical connections and less expense in the cartridge 314. In addition, disassembly of the cartridge 314 is not necessarily required in order for the device to be sterilized.

In another alternate embodiment of an automated system 10 for loading low dose radioisotope seeds into a plurality of implant needles multiple replaceable cartridges may be utilized in place of the single replaceable cartridge 14. For example, one cartridge could only contain radioisotope seeds and another cartridge could contain material for spacers and plugs, although separate cartridges for each is also contemplated. Multiple cartridges may be configured like cartridge 14 having internal stepper motors and circuitry, or may be configured like cartridge 314 having external stepper motors and circuitry. The advantage of multiple cartridges is that a smaller rotatable drum may be utilized for each cartridge, thereby increasing the indexing speed and the separation of seeds and spacers into separate cartridges can simplify the combinatorial arrangements of seeds and spacers. Preferably, the cartridges would be positioned in longitudinal sequential order relative to the path of travel of the push rod such that a seed and spacer are loaded together from the multiple cartridges on a single pass of the push rod.

Alternatively, instead of providing individual spacers, one of the cartridges could supply a source of material from which the loading station creates spacers and/or plugs to be selectively ejected by the automated motion control system into each of the needles. Because the spacers and plugs are made of relatively long lasting material such as suture or polymer material, this embodiment allows for a source of the material for the spacers or plugs to be supplied separately from supply of the time critical radioisotope seeds. In the case of the spacers, for example, it would be possible to provide a continuous coil of suture material as part of a replaceable cartridge with mechanisms to dispense and cut the appropriate lengths of suture material as part of a replaceable cartridge or loading station. Alternatively, a replaceable cartridge or compartment in loading station may be loaded with a bulk quantity of plugs that are oriented and advanced into the proper positioning by mechanisms within the loading station.

In another alternate embodiment, the number of cartridges is made equal to the greatest number of radioisotope seeds to be loaded into a single implant needle such that all of the seeds and spacers for a single needle could be simultaneously loaded on a single pass of the push rod. In another alternate embodiment, multiple push rods could be used with the multiple cartridges having multiple apertures to load multiple needles at the same time.

It should be understood that in the broadest sense, the automated motion control system of the present invention encompasses the various motors, actuators, encoders, detectors and feedback circuits that accomplish the controlled motion required to load the implant needles automatically and without manual intervention. It will be recognized by a person of ordinary skill in the art that numerous variations in the arrangement of motors, actuators, encoders, detectors and feedback circuits can be made and still accomplish the function of loading the implant needles automatically, such as belt driven systems or screw-drive powered systems instead of direct motor driven systems, mechanical or electrical encoders and detectors instead of optical encoders and detectors, and linear actuators instead of rotary actuators or vice versa.

Although the preferred embodiment of the automated system of the present invention has been described, it will be recognized that numerous changes and variations can be made and that the scope of the present invention is intended to be defined by the claims.

What is claimed is:

1. An automated implantation system for implanting low dose radioisotope seeds in a patient as part of a brachytherapy procedure comprising:

a storage structure adapted to hold a plurality of radioisotope seeds;

a needle assembly;

a Z-axis automated motion control system that selectively moves at least the needle assembly along an insertion axis and into the patient and selectively ejects radioisotope seeds from the storage structure into the needle assembly;

an X-Y axis automated motion control system that selectively moves at least the needle assembly in a plane perpendicular to the insertion axis to selectively position the insertion axis relative to the patient, and a computer processor operably connected to at least the Z-axis automated motion control system and the X-Y axis automated motion control system and having a user interface that displays information about the automated implantation system and accepts commands from a user to control the process of implanting the plurality of radioisotope seeds in the patient, wherein the user interface displays a grid identifying a plurality of locations that are selectable by the user in the plane perpendicular to the insertion axis where radioisotope seeds are to be implanted and the computer processor controls the X-Y axis automated motion control system to position at least the needle assembly perpendicular to a location selected by the user, wherein the storage structure is a replaceable cartridge and the system include cartridge receiving structure defined along at least a portion of the insertion axis.

2. The automated implantation system of claim 1 wherein the Z axis automated motion control system moves the cartridge and the needle assembly together to maintain a relative position between the cartridge and the needle assembly along the insertion axis.

3. The automated implantation system of claim 1, wherein computer process selectively rotates the grid within the plane perpendicular to the insertion axis so as to simulate a rotation of the needle assembly with respect to the plane perpendicular to the insertion axis and then recomputes the locations selected by the user in response to the rotation to achieve the rotation without requiring that the needle assembly be physically rotated in the plane perpendicular to the insertion axis.

4. The automated implantation system of claim 1, wherein the user interface includes at least one direction control input mechanism that allows a user to selectively control at least the Z-axis automated motion control system to control movement of at least the needle assembly along the insertion axis and into the patient.

5. The automated implantation system of claim 4 wherein the direction control input mechanism is a joystick.

6. An automated implantation system for implanting low dose radioisotope seeds in a patient as part of a brachytherapy procedure comprising:

a storage structure adapted to hold a plurality of radioisotope seeds;

a needle assembly;

an ultrasound probe;

a first Z-axis automated motion control system that selectively moves at least the needle assembly along an insertion axis and into the patient and selectively ejects radioisotope seeds from the storage structure into the needle assembly;

a second Z-axis automated motion control system that selectively moves the ultrasound probe in a probe axis generally parallel to the insertion axis;

a computer processor operably connected to at least the second Z-axis automated motion control systems and to the ultrasound probe such that the computer processor utilizes the ultrasound probe to monitors a position of an organ being treated in the brachytherapy procedure and selectively adjusts a base plane position of the insertion axis relative to the organ, and an autofocus system operably connected to the ultrasound probe and the second Z axis automated motion control system such that the computer processor utilizes the autofocus system to automatically adjust the base plane position.

7. The automated implantation system of claim 6 wherein the computer processor automatically adjusts the base plane in response to a movement in the position of the organ during the brachytherapy procedure.

8. The automated implantation system of claim 6 wherein the computer processor adjusts the base plane in response to a user directive and all subsequent radioisotope seeds placed by the implantation systems are placed at a depth determined from the adjusted base plane position.

9. An automated implantation system for implanting low dose radioisotope seeds in a patient as part of a brachytherapy procedure comprising:

a storage structure adapted to hold a plurality of radioisotope seeds;

a needle assembly;

a first Z-axis automated motion control system that selectively moves at least the needle assembly along an insertion axis and into the patient and selectively ejects radioisotope seeds from the storage structure into the needle assembly;

an ultrasound probe;

a second Z-axis automated motion control system that selectively moves the ultrasound probe in a probe axis generally parallel to the insertion axis; and a computer processor operably connected to at least the second Z-axis automated motion control system that executes an autocalibration routine that automatically calibrates the second Z-axis automated motion control system prior to utilizing the ultrasound probe in the brachytherapy procedure.

10. The automated implantation system of claim 9 wherein the ultrasound probe is replaceable and the computer processor determines an XYZ relationship of the ultrasound sound probe to the needle assembly each time a different replaceable ultrasound probe is used with the automated implantation system.

11. An automated implantation system for implanting low dose radioisotope seeds in a patient as part of a brachytherapy procedure comprising:

a storage structure adapted to hold a plurality of radioisotope seeds;

a needle assembly including a needle coaxially located within a canula;

a needle automated motion control system that controls the needle; and a canula automated motion control system that controls the canula separately from the needle, such that the needle automated motion control system and the canula automated motion control system cooperate to initially move the needle and canula along an insertion axis and into the patient and the needle automated motion control system withdraws the needle to selectively ejects radioisotope seeds from storage structure into the canula.

12. The automated implantation system of claim 11 wherein the needle automated motion control system and the canula automated motion control system initially move the needle and canula along the insertion axis by repetitively advancing the needle a distance beyond the canula and then advancing the canula that same distance.

13. The automated implantation system of claim 12 wherein the distance the needle automated motion control system advances the needle beyond the canula ranges between 0.5 and 2.0 cm.

14. The automated implantation system of claim 11 wherein the canula automated motion control system withdraws the canula once all the radioisotope seeds are positioned in the patient with the needle automated motion control system keeping the needle in place until the canula is withdrawn.

15. The automated implantation system of claim 11 wherein the storage structure further includes a plurality of spacers and wherein the needle automated motion control system selectively ejects a radioisotope seed and a spacer into the canula as a pair oriented longitudinally along the insertion axis and advances the pair along the insertion axis by pushing on the spacer with the needle.

16. The automated implantation system of claim 15 wherein the needle automated motion control system withdraws the needle once the canula is positioned as desired to accept a plurality of pairs each consisting of a radioisotope seed and a spacer in the canula and each pair is moved along the insertion axis to a staging area in the canula proximal to a distal end of the canula until all of the pairs for a current location of the canula are in the staging area after which the needle automated motion control system advances all of the pairs along the insertion axis to the distal end of the canula.

17. The automated implantation system of claim 16 wherein the canula automated motion control system withdraws the canula once all the pairs are positioned at the distal end of the canula with the needle automated motion control system keeping the needle in place until the canula is withdrawn.

18. The automated implantation system of claim 16 wherein the canula includes at least one annular wiping seal positioned along the insertion axis at an end of the staging area.

19. The automated implantation system of claim 11 wherein the needle automated motion control system and the canula automated motion control system comprise a pair of synchronized lead screw drives.

20. The automated implantation system of claim 11 wherein the needle automated motion control system comprises a capstan drive system and the canula automated motion control system comprises a lead screw drive.

21. The automated implantation system of claim 11 wherein the needle is selectively replaceable in the needle automated motion control system.

22. An automated implantation system for implanting low dose radioisotope seeds in a patient as part of a brachytherapy procedure comprising:
   a storage structure adapted to hold a plurality of radioisotope seeds;
   a needle assembly;
   a Z-axis automated motion control system that selectively moves at least the needle assembly along an insertion axis and into the patient and selectively ejects radioisotope seeds from the storage structure into the needle assembly;
   a targeting indication system that demarks a location of where the insertion axis is positioned on the patient during a brachytherapy procedure; and
   at least a plurality of light emitting devices that generate a corresponding plurality of light beams on the location.

23. An automated implantation system for implanting low dose radioisotope seeds in a patient as part of a brachytherapy comprising:
   a storage structure adapted to hold a plurality of radioisotope seeds;
   a needle assembly;
   a Z-axis automated motion control system that selectively moves at least the needle assembly along an insertion axis and into the patient and selectively ejects radioisotope seeds from the storage structure into the needle assembly; and
   a base station that supports at least the Z-axis automated motion control system and the needle assembly and positions the insertion axis relative to the patient, the base station including:
      a base;
      a moveable assembly that includes the insertion axis and is orientable independently of the base; and
      a stand operably connected between the base and the moveable assembly wherein the stand includes:
         a gross vertical adjustment mechanism that adjusts a vertical height of the moveable assembly relative to the base;
         a rotation mechanism that pivots the moveable assembly about a vertical axis relative to the base;
         a lateral positioning mechanism that adjusts a lateral position of the moveable assembly in relation to the vertical axis; and
         a tilt mechanism that tilts the moveable assembly relative to a horizontal plane perpendicular to vertical axis.

24. The automated implantation system of claim 23 wherein at least the gross vertical adjustment mechanism is motorized.

25. The automated implantation system of claim 23 wherein the base includes a set of retractable wheels that allows the implantation system to be moved when the wheels are extended and provide a stable position for the implantation system when the wheels are withdrawn.

26. The automated implantation system of claim 23 wherein the base station includes alternative power sources, a primary power source that plugs into an external outlet and a secondary power source connected to a battery housed in the base station, the secondary power source configured to replace the primary power source in the event that the primary power source is unplugged from the external outlet.

27. An automated implantation system for implanting low dose radioisotope seeds in a patient as part of a brachytherapy procedure comprising:
   a storage structure adapted to hold a plurality of radioisotope seeds;
   a needle assembly;
   an ultrasound probe having an outer rigid sheath coaxial with the ultrasound probe;
   a first Z-axis automated motion control system that selectively moves at least the needle assembly along an insertion axis and selectively ejects radioisotope seeds from the storage structure into the needle assembly;
   a second Z-axis automated motion control system that selectively moves the ultrasound probe in a probe axis generally parallel to the insertion axis such that the second Z-axis automated motion control system initially positions both the outer sheath and the ultrasound probe in the patient and then moves only the ultrasound probe along the probe axis and within the sheath to generate ultrasound images along the probe axis.

28. An automated implantation system for implanting low dose radioisotope seeds in a patient as part of a brachytherapy procedure comprising:
   cartridge receiving structure adapted to receive a cartridge containing a plurality of radioisotope seeds;
   a needle assembly;
   carrier receiving structure adapted to receive a carrier structure containing an ultrasound probe;

a first Z-axis automated motion control system that selectively moves at least the needle assembly along an insertion axis and selectively ejects radioisotope seeds from the storage structure into the needle assembly;

a second Z-axis automated motion control system that selectively moves the ultrasound probe in a probe axis generally parallel to the axis of insertion.

29. The automated implantation system of claim 28 wherein the carrier structure includes a mechanism to allow for rotation of the ultrasound probe relative to the probe axis and to selectively lock the ultrasound probe in a desired rotation.

30. The automated implantation system of claim 28 wherein the needle assembly and the cartridge are operably arranged in a common carrier structure and the carrier structure mates with a cartridge receiving structure.

31. A method of operating an automated implantation system having a Z-axis automated motion control system and an X-Y axis automated motion control system that control at least a needle assembly for implanting low dose radioisotope seeds in a patient as part of a brachytherapy procedure comprising:

(a) using the X-Y axis automated motion control system to position an insertion axis of the needle assembly relative to the patient;

(b) using the Z-axis automated motion control system to selectively move the needle assembly along the insertion axis to implant at least one radioisotope seed wherein the needle assembly comprises a needle coaxially located within a canula and wherein the Z-axis automated motion control system comprises a needle automated motion control system that controls the needle and a canula automated motion control system that controls the canula and step (b) comprises:

(b1) using the needle automated motion control system and the canula automated motion control system to repetitively advancing the needle a distance beyond the canula along the insertion axis and then advancing the canula that same distance until the canula is positioned at a desired depth relative to the base plane;

(b2) using the needle automated motion control system to withdraw the needle once the canula is positioned at the desired depth to accept a radioisotope seed and then advancing the needle to position the radioisotope seed in the canula; and (c) repeating steps (a) and (b) for a plurality of locations on a base plane perpendicular to the insertion axis.

32. A method of operating an automated system for inserting a needle assembly for implanting low dose radioisotope seeds in a patient as part of a brachytherapy procedure, the needle assembly comprising a needle coaxially located within a canula and the automated system comprising a needle automated motion control system that controls the needle and a canula automated motion control system that controls the canula, the method comprising:

(a) positioning the needle assembly along an insertion axis relative to the patient;

(b) using the needle automated motion control system and the canula automated motion control system to repetitively advancing the needle a distance beyond the canula along the insertion axis and then advancing the canula that same distance until the canula is positioned at a desired depth; and (c) using the needle automated motion control system to withdraw the needle once the canula is positioned at the desired depth to accept a radioisotope seed and then advancing the needle to position the radioisotope seed in the canula.

33. The method of claim 32 wherein step (b) is performed such that the distance the needle automated motion control system advances the needle beyond the canula ranges between 0.5 and 2.0 cm.

34. The method of claim 32 further comprising:

(d) using the canula automated motion control system to withdraw the canula once the radioisotope seed is positioned with the needle automated motion control system keeping the needle in place until the canula is withdrawn.

35. The method of claim 32 wherein automated system includes at least one cartridge containing a plurality of radioisotopes seeds and a plurality of spacers and wherein step (c) is performed such that a radioisotope seed and a spacer are ejected from the cartridge into the canula as a pair oriented longitudinally along the insertion axis and needle automated motion control system advances the pair along the insertion axis by pushing on the spacer with the needle.

36. An automated implantation system for implanting low dose radioisotope seeds in a patient as part of a brachytherapy procedure comprising:

means for storing at least a plurality of radioisotope seeds;

a needle assembly;

an ultrasound probe;

first automated means for selectively moving at least the needle assembly along an insertion axis;

second automated means for selectively moving the ultrasound probe in a probe axis generally parallel to the insertion axis; and a computer processor means operably connected to at least the second automated means and to the ultrasound probe for monitoring a position of an organ being treated in the brachytherapy procedure and selectively adjusting a base plane position of the insertion axis relative to the organ.

37. An automated implantation system for implanting low dose radioisotope seeds in a patient as part of a brachytherapy procedure comprising:

means for storing at least a plurality of radioisotope seeds;

a needle assembly;

an ultrasound probe;

a first automated means for selectively moving at least the needle assembly along an insertion axis and for selectively ejecting radioisotope seeds from the storage structure into the needle assembly;

a second automated means for selectively moving the ultrasound probe in a probe axis generally parallel to the insertion axis; and a computer processor operably connected to at least the second automated means, including means for automatically calibrating the second automated means prior to utilizing the ultrasound probe in the brachytherapy procedure.

38. An automated implantation system for implanting low dose radioisotope seeds in a patient as part of a brachytherapy procedure comprising:

means for storing at least a plurality of radioisotope seeds;

a needle coaxially located within a canula;

first automated means for controlling movement of the needle along an insertion axis; and second automated means for controlling movement of the canula along the insertion axis.

39. An automated implantation system for implanting low dose radioisotope seeds in a patient as part of a brachytherapy procedure comprising:
  means for storing at least a plurality of radioisotope seeds;
  a needle assembly;
  automated means for selectively moving at least the needle assembly along an insertion axis and selectively ejecting radioisotope seeds from the means for storing into the needle assembly; and
  a base station that supports at least the automated means and the needle assembly and positions the insertion axis relative to the patient, the base station including:
    a base;
    a moveable assembly that includes the insertion axis; and
    means operably connected between the base and the moveable assembly for orienting the moveable assembly independently of the base, including:
      means for adjusting a vertical height of the moveable assembly relative to the base;
      means for pivoting the moveable assembly about a vertical axis relative to the base;
      means for adjusting a lateral position of the moveable assembly in relation to the vertical axis; and
      means for tilting the moveable assembly relative to a horizontal plane perpendicular to the vertical axis.

40. An automated implantation system for implanting low dose radioisotope seeds in a patient as part of a brachytherapy procedure comprising:
  cartridge receiving structure adapted to receive a cartridge containing a plurality of radioisotope seeds;
  a needle assembly;
  carrier receiving structure adapted to receive a carrier structure containing an ultrasound probe;
  first automated means for selectively moving at least the needle assembly along an insertion axis and selectively ejecting radioisotope seeds from the cartridge;
  second automated means for selectively moving the ultrasound probe in a probe axis generally parallel to the axis of insertion.

41. An automated system for controlling insertion of a needle assembly into a patient along an insertion axis, the needle assembly having a needle coaxially located within a canula, the automated system comprising:
  base structure that positions the insertion axis relative to the patient, the base structure having a base, a moveable assembly that is orientable independently of the base and includes structure defined along a portion of the insertion axis to receive the needle assembly and, and structure operably connected between the base and the moveable assembly;
  a Z-axis automated motion control system that selectively moves the needle assembly along the insertion axis when the needle assembly is positioned in the moveable assembly, wherein the Z-axis automated motion control system comprises:
    a needle automated motion control system that controls the needle; and
    a canula automated motion control system that controls the canula;
  an X-Y axis automated motion control system that selectively moves at least the needle assembly in a plane perpendicular to the insertion axis; and
  a computer processor operably connected to at least the Z-axis automated motion control system and the X-Y axis automated motion control system and having a user interface that displays information about the automated implantation system and accepts commands from a user to control the process of inserting the needle assembly.

42. The automated system of claim 41 wherein the needle automated motion control system and the canula automated motion control system cooperate to initially move the needle and canula along the insertion axis by repetitively advancing the needle a distance beyond the canula and then advancing the canula that same distance.

43. The automated system of claim 41 wherein the needle automated motion control system and the canula automated motion control system comprise a pair of synchronized lead screw drives.

44. The automated system of claim 41 wherein the needle assembly includes a force sensor operably connected to at least the needle and to the needle automated motion control system.

45. The automated system of claim 44 wherein the force sensor senses whether the needle encounters resistance above an expected force for piercing tissue when the needle automated motion control system advances the needle and, in response, the needle automated motion control system stops advancing the needle.

46. The automated system of claim 45 wherein the force sensor comprises a load cell mounted in a compliant mount at a rear of capstan drive assembly that moves the needle, the compliant mount providing with a minimum travel distance in the event that the needle encounters resistance above the expected force for piercing tissue that forms a safety buffer to allow the needle to retract.

47. The automated system of claim 44 wherein the force sensor senses whether the needle has advanced into a non-tissue region and, in response, provides an indication to a user via the user interface that the needle has advanced into the non-tissue region.

48. A method of operating an automated system for inserting a needle assembly in a patient as part of a medical procedure, the needle assembly comprising a needle coaxially located within a canula and the automated system comprising a needle automated motion control system that controls the needle, a canula automated motion control system that controls the canula and a force sensor operably connected to at least the needle and to the needle automated motion control system, the method comprising:
  (a) positioning the needle assembly along an insertion axis relative to the patient;
  (b) using the needle automated motion control system and the canula automated motion control system to repetitively advancing the needle a distance beyond the canula along the insertion axis and then advancing the canula that same distance until the canula is positioned at a desired depth; and
  (c) in the event that the force sensor senses the needle has encountered resistance above an expected force for piercing tissue when the needle automated motion control system advances the needle in step (b), using the needle automated motion control system to stops advancing the needle.

* * * * *